(12) United States Patent
Nishino et al.

(10) Patent No.: US 8,107,590 B2
(45) Date of Patent: Jan. 31, 2012

(54) PORTABLE RADIOGRAPHIC IMAGING APPARATUS AND RADIOGRAPHIC IMAGE MANAGEMENT APPARATUS

(75) Inventors: Naoyuki Nishino, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 132 days.

(21) Appl. No.: 12/545,092

(22) Filed: Aug. 21, 2009

(65) Prior Publication Data

US 2010/0054417 A1   Mar. 4, 2010

(30) Foreign Application Priority Data

Aug. 28, 2008   (JP) .................... 2008-219385

(51) Int. Cl.
  *H05G 1/64* (2006.01)
  *G01N 23/083* (2006.01)
(52) U.S. Cl. ............... 378/98.8; 378/62; 250/370.09
(58) Field of Classification Search .......... 378/98.8, 378/189, 62; 250/370, 370.09, 9
See application file for complete search history.

(56) References Cited

U.S. PATENT DOCUMENTS

| | | | | |
|---|---|---|---|---|
| 5,877,501 A * | 3/1999 | Ivan et al. | .............. | 250/370.09 |
| 6,344,652 B1 * | 2/2002 | Shoji | .............. | 250/370.09 |
| 6,433,341 B1 * | 8/2002 | Shoji | .............. | 250/370.09 |
| 6,590,958 B2 * | 7/2003 | Barber et al. | .............. | 378/98.8 |
| 6,630,676 B2 * | 10/2003 | Takemoto | .............. | 250/370.09 |
| 7,006,600 B1 * | 2/2006 | Krema et al. | .............. | 378/98.7 |
| 7,109,491 B2 * | 9/2006 | Shinden | .............. | 250/370.09 |
| 7,119,841 B1 * | 10/2006 | Sako | .............. | 348/333.05 |
| 7,247,859 B2 * | 7/2007 | Murphy et al. | .............. | 250/370.09 |
| 7,250,608 B2 * | 7/2007 | Ozeki | .............. | 250/370.09 |
| 7,359,483 B2 * | 4/2008 | Koshiji | .............. | 378/116 |
| 7,365,337 B2 * | 4/2008 | Tsuchino et al. | .............. | 250/370.09 |
| 7,406,150 B2 * | 7/2008 | Minyard et al. | .............. | 378/37 |
| 7,545,914 B2 * | 6/2009 | Kito et al. | .............. | 378/98.8 |
| 7,573,034 B2 * | 8/2009 | Heath et al. | .............. | 250/361 R |
| 7,593,507 B2 * | 9/2009 | Ohta et al. | .............. | 378/98.8 |
| 7,924,980 B2 * | 4/2011 | Ohta et al. | .............. | 378/98.8 |

FOREIGN PATENT DOCUMENTS

| | | |
|---|---|---|
| JP | 7-246199 A | 9/1995 |
| JP | 2000-262504 A | 9/2000 |
| JP | 2004-097543 A | 4/2004 |
| JP | 2004-097635 A | 4/2004 |
| JP | 2006-150078 A | 6/2006 |

* cited by examiner

*Primary Examiner* — Allen C. Ho
(74) *Attorney, Agent, or Firm* — SOLARIS Intellectual Property Group, PLLC

(57) ABSTRACT

There is provided a portable radiographic imaging apparatus including: an image output unit which detects a radiation which penetrates an object to be imaged and is irradiated on a surface to be irradiated of a casing, and outputs data of a radiographic image which represents a distribution of an amount of irradiated radiation; a first storage unit which stores the data of the radiographic image output from the image output unit; a display unit which displays an image; and a display control unit which allows the display unit to display a previously captured radiographic image which is associated with a current imaging, before the object to be imaged is imaged.

8 Claims, 13 Drawing Sheets

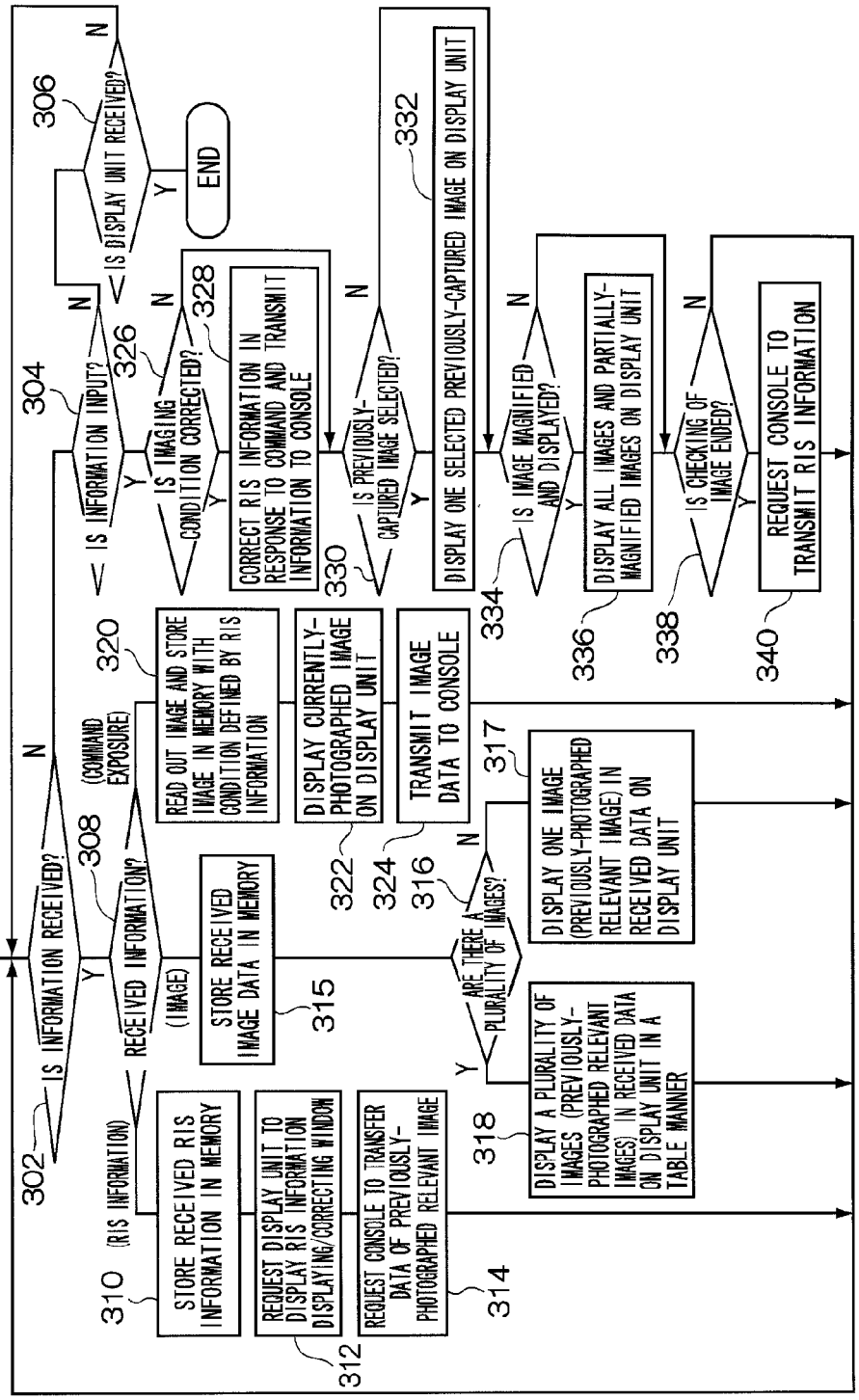

RIS INFORMATION DISPLAYING/CORRECTING WINDOW

```
PATIENT NAME ○○ ○○
PATIENT ID ×××××××
RADIOGRAPHIC IMAGING HISTORY
YEAR:○○ MONTH:△△ DATE:×× CHEST IMAGING
IMAGING CONDITION
  IMAGED PORTION    CHEST
  IMAGING POSTURE  [ERECT POSITION ▼]
  TUBE VOLTAGE     [○○ kV ▼]
  TUBE CURRENT     [△ A ▼]
```

PREVIOUSLY-CAPTURED IMAGE TABLE DISPLAY WINDOW

CURRENTLY-CAPTURED IMAGE DISPLAY WINDOW

PARTIALLY MAGNIFYING/DISPLAYING WINDOW

PORTABLE RADIOGRAPHIC IMAGING APPARATUS AND RADIOGRAPHIC IMAGE MANAGEMENT APPARATUS

CROSS-REFERENCE TO RELATED APPLICATION

This application is based on and claims priority under 35 USC 119 from Japanese Patent Application No. 2008-219385 filed on Aug. 28, 2008, the disclosure of which is incorporated by reference herein.

BACKGROUND

1. Technical Field

The present invention relates to a portable radiographic imaging apparatus and a radiographic image management apparatus, and more particularly, to a portable radiographic imaging apparatus having an image output unit which detects a radiation penetrating a to-be-imaged object to be irradiated on a to-be-irradiated surface of a casing and outputs data of a radiographic image indicating a distribution of an amount of irradiated radiation and a radiographic image management apparatus having a storage unit which stores data of a previously-captured radiographic image, which may communicate with a portable radiographic imaging apparatus having a display unit which may display an image.

2. Related Art

Recently, a flat panel detector (FPD) that is configured by disposing a radiation sensitive layer on a thin film transistor (TFT) active matrix substrate has been put to practical applications. The FPD detects an irradiated radiation such as an x-ray and directly converts the amount of irradiated radiation into data of a radiographic image indicating a distribution of the amount of irradiated radiation. A portable radiographic imaging apparatus (hereinafter, referred to as an "electronic cassette") including such as an FPD and storing data of a radiographic image output from the FPD has been put to practical applications. Since the electronic cassette has a good portability, a patient on a stretcher or a bed may be image captured. In addition, since a portion to be image may be easily adjusted by changing a position of the electronic cassette, an immobile patient may be adaptively image captured.

Recently, an electronic cassette added with a display unit capable of checking the captured radiographic image at the imaging site has been proposed. For example, JP-A No. 2000-262504 discloses a radiation detecting cassette having a detector for detecting a radiation penetrating a patient and a display unit such as a LCD panel which is disposed on a rear side of the cassette.

In addition, JP-A No. 7-246199 discloses an X-ray diagnosis apparatus which is configured by laminating an upper cover, an X-ray grid, a flat panel detector, a digital X-ray information storage unit, a flat LCD unit, and a lower cover. An X-ray image displayed on the LCD unit may be viewed from a rear surface of the apparatus.

In addition, JP-A No. 2006-150078 discloses a configuration where a reference display unit capable of displaying an image is installed in a housing of a digital image detector (refer to FIG. 2 of JP-A No. 2006-150078), a configuration where the reference display unit is detachably installed in the housing and mechanically or electrically coupled with an electrical interface disposed on a wall of the housing (refer to FIG. 3 of JP-A No. 2006-150078), and a configuration where the reference display unit is installed separately from the housing and wirelessly communicate with the digital image detector (refer to FIG. 4 of JP-A No. 2006-150078).

In addition, JP-A No. 2004-97543 discloses a configuration where an image display unit made of a material having a high x-ray permeability is fixed to a position neighboring a body surface of a to-be-tested man by a supporting mechanism.

In addition, JP-A No. 2004-97635 discloses a configuration where a control apparatus having an image display unit, a manipulator, and a communication unit capable of performing wireless communication is disposed separately from an X-ray imaging apparatus. The X-ray imaging apparatus may be disposed to a position where an operator may easily operate, by using mount-angle changeable legs.

In the radiographic imaging, if the patient moves at the time of the imaging, blur of the image captured object may occur in the radiographic image. In this case, the imaging needs to be performed again. In any one of JP-A Nos. 2000-262504, 7-246199, 2006-150078, 2004-97543, and 2004-97635, since the display unit is added to the electronic cassette or since the display unit is disposed in the vicinity of the electronic cassette, the radiographic image obtained by the imaging is displayed on the display unit. After the radiographic imaging, by referring to the radiographic image displayed on the display unit, it may be directly checked by a user (imaging operator) whether or not the image captured object blur occurs in the captured radiographic image.

In addition, in the radiographic imaging, in a case where the radiographic imaging was performed previously on the same portion of the same patient, in order to facilitate surgeon's reading of the radiographic image, there is a need in that the imaging range (positioning) of the current imaging is equal to that of the previously-captured radiographic image, if possible. However, the techniques disclosed in JP-A Nos. 2000-262504, 7-246199, 2006-150078, 2004-97543, and 2004-97635 do not satisfy the need, and it is difficult for the user to grasp the imaging range of the previously-captured radiographic image in the imaging room. Therefore, there is a problem in that the accuracy of the process of adjusting the imaging range by the user is not satisfactory.

SUMMARY

In view of the above problems in the related art, the invention provides a portable radiographic imaging apparatus and a radiographic image management apparatus capable of improving an accuracy of an operation of adjusting an imaging range at the time of capturing a radiographic image.

In order to achieve the object, one aspect of the present invention provides a portable radiographic imaging apparatus including:

an image output unit which detects a radiation which penetrates an object to be imaged and is irradiated on a surface to be irradiated of a casing, and outputs data of a radiographic image which represents a distribution of an amount of irradiated radiation;

a first storage unit which stores the data of the radiographic image output from the image output unit;

a display unit which displays an image; and a display control unit which allows the display unit to display a previously captured radiographic image which is associated with a current imaging, before the object to be imaged is imaged.

The display unit may have a configuration such that the display surface capable of displaying the image may be expanded outside the casing and the display unit is disposed to the casing so that receiving of the display surface inside the casing or folding of the display surface may be performed or a configuration such that the information of the to-be-displayed object is projected and displayed on the projected object irradiated with the projecting light by emitting the projecting light for projecting and displaying the information of the to-be-displayed object.

In addition, the display control unit may be configured so that the previously-captured radiographic image associated with the current imaging is unconditionally displayed, for example, in a time duration before the object is imaged. Alternatively, the display control unit may be configured so that the displaying is performed only if the displaying of the previously-captured radiographic image is instructed through a command unit or only if the displaying of the previously-captured radiographic image is set in advance.

In this manner, since the previously-captured radiographic image associated with the current imaging is displayed by the display unit before the object is imaged, the user may grasp the imaging range of the displayed radiographic image by referring to the radiographic image displayed by the display unit. Therefore, the user may adjust the imaging range of the current imaging by referring to the displayed radiographic image so as to be equal to the imaging range of the displayed radiographic image. Accordingly, it is possible to improve the accuracy of the process of adjusting the imaging range at the time of the radiographic imaging.

In addition, in a case where the data of the previously-captured radiographic image is stored in the second storage unit installed in the radiographic image management apparatus, the communication unit that may communicate with the radiographic image management apparatus is provided, so that the display control unit may receive the data of the radiographic image associated with the current imaging among the previously-captured radiographic image stored in the management apparatus, through the communication unit from the radiographic image management apparatus and allow the display unit to display the received data as the radiographic image associated with the current imaging.

In the configuration, by transmitting the data of the radiographic image obtained by performing the radiographic imaging from the portable radiographic imaging apparatus to the radiographic image management apparatus, the data of the previously-captured radiographic image is stored in the second storage unit of the radiographic image management apparatus. Therefore, even in a system where a plurality of the portable radiographic imaging apparatuses are installed, the data of the previously-captured radiographic images may be managed in the radiographic image management apparatus in a unified manner. Accordingly, even in a case where the previously-captured radiographic image associated with the current imaging is a radiographic image captured by using another portable radiographic imaging apparatus, the data of the radiographic image may be easily obtained.

In addition, although the determination of the previously-captured radiographic image associated with the current imaging may be performed by the radiographic image management apparatus, the display control unit may set a condition of the radiographic image associated with the current imaging based on attribute information indicating an attribute of the current imaging and notifies the set condition to the radiographic image management apparatus through the communication unit to request the radiographic image management apparatus to transmit the data of the previously-captured radiographic image associated with the current imaging.

In addition, the data of the previously-captured radiographic image may be stored in the first storage unit. In this case, the display control unit may search for the data of the radiographic image associated with the current imaging among the data of the previously-captured radiographic image stored in the first storage unit to read out from the first storage unit the data of the radiographic image extracted by the searching and allow the display unit to display the read-out data as the radiographic image associated with the current imaging. In this configuration, since the radiographic image management apparatus or the like may be omitted, the configuration is very suitable for a small-sized system (for example, a system installed with only one portable radiographic imaging apparatus).

In addition, the display control unit may set a condition of the radiographic image associated with the current imaging based on attribute information indicating an attribute of the current imaging and search for the data of the radiographic image associated with the current imaging based on the set condition.

In addition, more specifically, as the previously-captured radiographic image associated with the current imaging, a radiographic image obtained from the previous imaging of the same imaged portion and the same imaged object as those of the current imaging may be adapted. In this case, the "condition of the radiographic image associated with the current imaging" becomes "the imaged portion and the imaged object are the same as those of the current imaging". As the previously-captured radiographic image associated with the current imaging, the radiographic image obtained from the previous imaging of the same imaged portion and the same imaged object as those of the current imaging is displayed by the display unit, and the radiographic image together with a radiographic image obtained from the current imaging is used for diagnosis by a surgeon. In addition, since the radiographic image is displayed by the display unit, the process of adjusting the imaging range may be performed so that the imaging range of the radiographic image obtained from the current imaging is accurately equal to the imaging range of the radiographic image, that is, so that the reading and diagnosis may be more easily performed by a surgeon.

In addition, as the previously-captured radiographic image associated with the current imaging, a radiographic image obtained from the previous imaging of the same imaged portion of an object to be imaged as that of the current imaging may be adapted. In this case, the "condition of the radiographic image associated with the current imaging" becomes "the imaged portion is the same as that of the current imaging". Although the object to be imaged of the radiographic image displayed by the display unit may not be the same as that of the current imaging, since the imaged portion of the radiographic image displayed by the display unit is the same of that of the current imaging, the imaging range of the current imaging may be adjusted so as to be equal to the imaging range of the radiographic image obtained from the previous imaging of the same imaged portion. Therefore, even in a case where there is no previously-captured radiographic image of which object to be imaged and imaged portion are the same as those of the current imaging (or a case where a specific portion of a patient is firstly imaged), the accuracy of the process of adjusting the imaging range may be improved.

In addition, an input unit installed on a casing or a display surface of the display unit may be further provided. In a case where there are a plurality of the previously-captured radiographic images associated with the current imaging, the display control unit may allow the display unit to reduce sizes of the plurality of the radiographic images and to display the plurality of the radiographic images in parallel. If information indicating which one of the plurality of radiographic images displayed in parallel is selected is input through the input unit, the display control unit may allow the display unit to magnify and display the selected radiographic images.

In addition, an imaging detecting unit which detects whether or not imaging is performed may be further provided. If imaging is detected by the imaging detecting unit, the display control unit may allow the display unit to display the radiographic image obtained from the current imaging or to display the radiographic image obtained from the current imaging and the previously-captured radiographic image associated with the current imaging in parallel.

In addition, another aspect of the present invention provides a radiographic image management apparatus including:

a communication unit capable of communicating with a portable radiographic imaging apparatus having a display unit capable of displaying an image;

a storage unit which stores data of previously captured radiographic images;

a searching unit which searches the radiographic images stored in the second storage unit for a radiographic image associated with a current imaging performed using the portable radiographic imaging apparatus; and an image transferring unit which transmits data of a radiographic image extracted by the searching of the searching unit to the portable radiographic imaging apparatus via the communication unit, so that the display unit displays the extracted radiographic image.

Therefore, the user may grasp the imaging range of the displayed radiographic image by referring to the radiographic image displayed by the display unit of the portable radiographic imaging apparatus. Therefore, the user may adjust the imaging range of the current imaging by referring to the displayed radiographic image so as to be equal to the imaging range of the displayed radiographic image. Accordingly, the accuracy of the process of adjusting the imaging range at the time of the radiographic imaging may be improved.

In addition, the condition of the radiographic image associated with the current imaging may be notified from the portable radiographic imaging apparatus in advance, and the searching for the radiographic image by the searching unit may be performed according to the notified condition. However, in a case where an attribute information notifying unit that transmits attribute information indicating an attribute of the current imaging performed by using the portable radiographic imaging apparatus through a communication unit to the portable radiographic imaging apparatus is provided, the searching unit may set the condition of the radiographic image associated with the current imaging based on the attribute information, and the searching for the data of the radiographic image associated with the current imaging may be performed according to the set condition. In this case, since the portable radiographic imaging apparatus needs not to set the condition of the radiographic image associated with the current imaging and notify the condition to the radiographic image management apparatus, a load on the portable radiographic imaging apparatus may be reduced and to reduce traffic between the radiographic image management apparatus and the portable radiographic imaging apparatus may also be reduced.

As described above, according to the invention, an excellent effect is obtained such that the accuracy of the process of adjusting the imaging range at the time of the radiographic imaging can be improved.

In addition, according to the invention, the radiographic image associated with the current imaging that is performed by using the portable radiographic imaging apparatus having the display unit that may display the image may be searched among the previously-captured radiographic image stored in the second storage unit, and the data of the radiographic image extracted by the searching may be transmitted to the portable radiographic imaging apparatus, so that the radiographic image is displayed by the display unit of the portable radiographic imaging apparatus. Accordingly, a good effect is obtained in that the accuracy of the process of adjusting the imaging range at the time of the radiographic imaging may be improved.

BRIEF DESCRIPTION OF THE DRAWINGS

FIG. 7 is a flowchart illustrating an example of details of an information displaying process performed in a cassette control unit of an electronic cassette;

DETAILED DESCRIPTION

Figure 1:
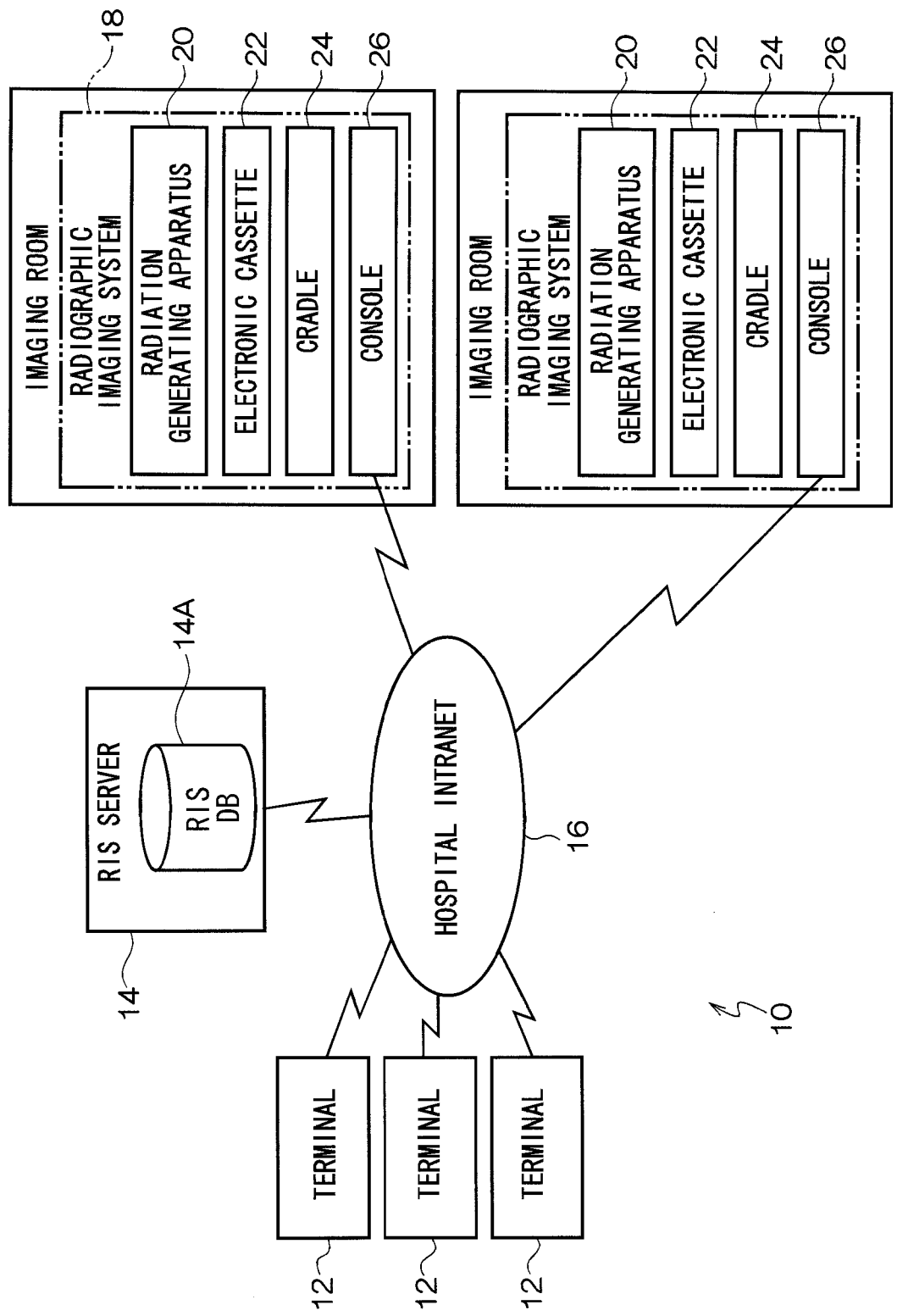
FIG. 1 is a block diagram illustrating a schematic configuration of a radiographic information system according to an exemplary embodiment.

Hereinafter, exemplary embodiments of the present invention will be described in detail with reference to the accompanying drawings. FIG. 1 illustrates a radiographic information system 10 (hereinafter, referred to as an "RIS 10") according to the exemplary embodiment. The RIS 10 is a system for performing information management such as diagnosis reservation and diagnosis recording in a department of radiology of a hospital. In the RIS 10, a plurality of terminals 12, an RIS server 14, and a radiographic imaging system 18 (a console 26 thereof) installed in each radiographic image capturing room (imaging room) (or a surgery room) in the hospital are connected to a hospital intranet 16 that is a wired or wireless local area network (LAN). The RIS 10 is configured as a portion of a hospital information system (HIS) in the same hospital. A HIS server (not shown) which controls a whole of the HIS is connected to the hospital intranet 16.

Each terminal 12 that is a personal computer (PC) or the like is manipulated by a doctor (a surgeon) or a radiological technologist. The surgeon or the radiological technologist inputs or searches for the diagnosis information or facility reservation information through the terminal 12. The request (that is, reservation) of capturing a radiographic image is also input through the terminal. 12. The RIS server 14 is a computer including a storage unit 14A (corresponding to a second storage unit disclosed in claim 12) for storing RIS database (DB). In the RIS database, registered are attribute information (for example, name, gender, date of birth, age, blood type, and patient ID) of a patient, a disease history, a medical examination history, a radiographic imaging history, and data of previously-captured radiographic images of the patient, and information (for example, a serial number, a type, a dimension, a sensitivity, an available imaged portion (details of available imaging request), a use starting date, a use times, and the like) of an electronic cassette 22 (described later) of each radiographic imaging system 18. The RIS server 14 performs processes of controlling the whole of the RIS 10 (for example, a process of controlling a schedule of capturing a radiographic image of each radiographic imaging system 18 that receives the imaging request from each terminal 12) based on the information registered in the RIS database.

Figure 2:
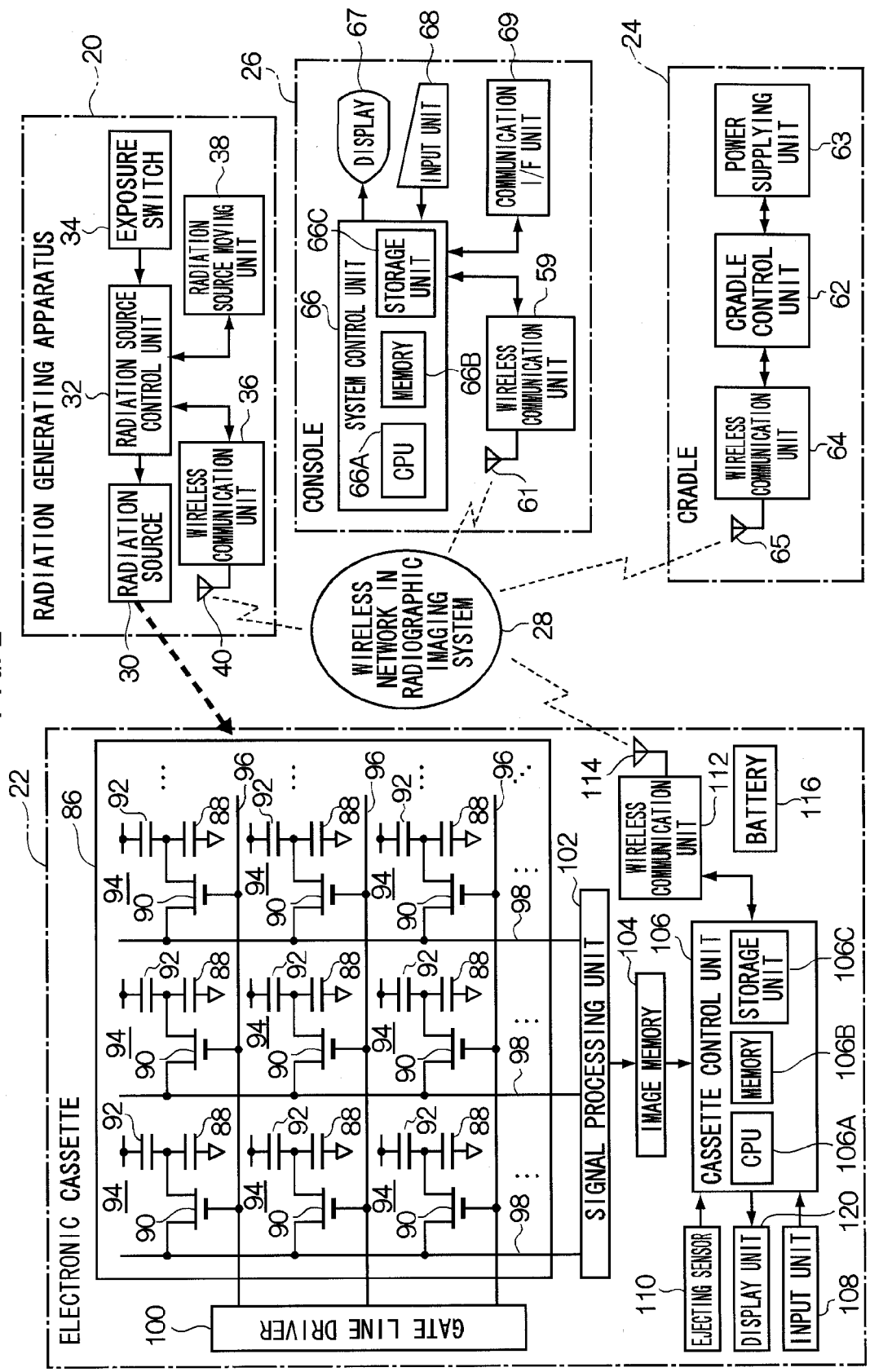
FIG. 2 is a block diagram illustrating a schematic configuration of a radiographic imaging system.

Each radiographic imaging system 18 is a system that performs capturing of a radiographic image in response to a command of the RIS server 14 according to manipulation of a surgeon or a radiological technologist. Each radiographic imaging system 18 includes a radiation generating apparatus 20 that generates a radiation to be irradiated on a patient (object to be imaged), an electronic cassette 22 having a radiation detector that detects the radiation penetrating the patient and outputs a converted radiographic image data, a cradle 24 that charges a battery 116 (refer to FIG. 2) embedded in the electronic cassette 22, and a console 26 that is used for controlling operations of each component. As shown in FIG. 2, since a wireless network 28 is installed in the radiographic imaging system 18, the radiation generating apparatus 20, the electronic cassette 22, the cradle 24, and the console 26 of the same radiographic imaging system 18 wirelessly transmit and receive various signals and information via the wireless network 28. The electronic cassette 22 corresponds to a portable radiographic imaging apparatus according to the invention.

The radiation generating apparatus 20 includes a radiation source 30 that has a radiation tube for generating a radiation through the radiation tube. The radiation source 30 is connected to a radiation source control unit 32. An exposure switch 34, a wireless communication unit 36, and a radiation source moving unit 38 are connected to the radiation source control unit 32. At the time of capturing a radiographic image, a user (radiological technologist) pushes the exposure switch 34. A wireless antenna 40 is connected to the wireless communication unit 36. The wireless communication unit 36 wirelessly communicates with other components of the same radiographic imaging system 18 through the wireless antenna 40 via the wireless network 28.

At the time of capturing the radiographic image, the radiation generating apparatus 20 receives from the console 26 imaging condition information indicating imaging conditions of the to-be-performed radiographic imaging. The received imaging condition information is input from the wireless communication unit 36 to the radiation source control unit 32. The imaging condition information received from the console 26 includes information indicating a radiation tube driving condition such as tube voltage or tube current of a radiation tube and irradiation time. When the exposure switch 34 is pushed, the radiation source control unit 32 controls the radiation source 30 so that the radiation tube of the radiation source 30 may be driven according to the driving condition. Accordingly, the radiation source 30 generates and emits a suitable amount of radiation corresponding to the driving condition.

Figure 3:
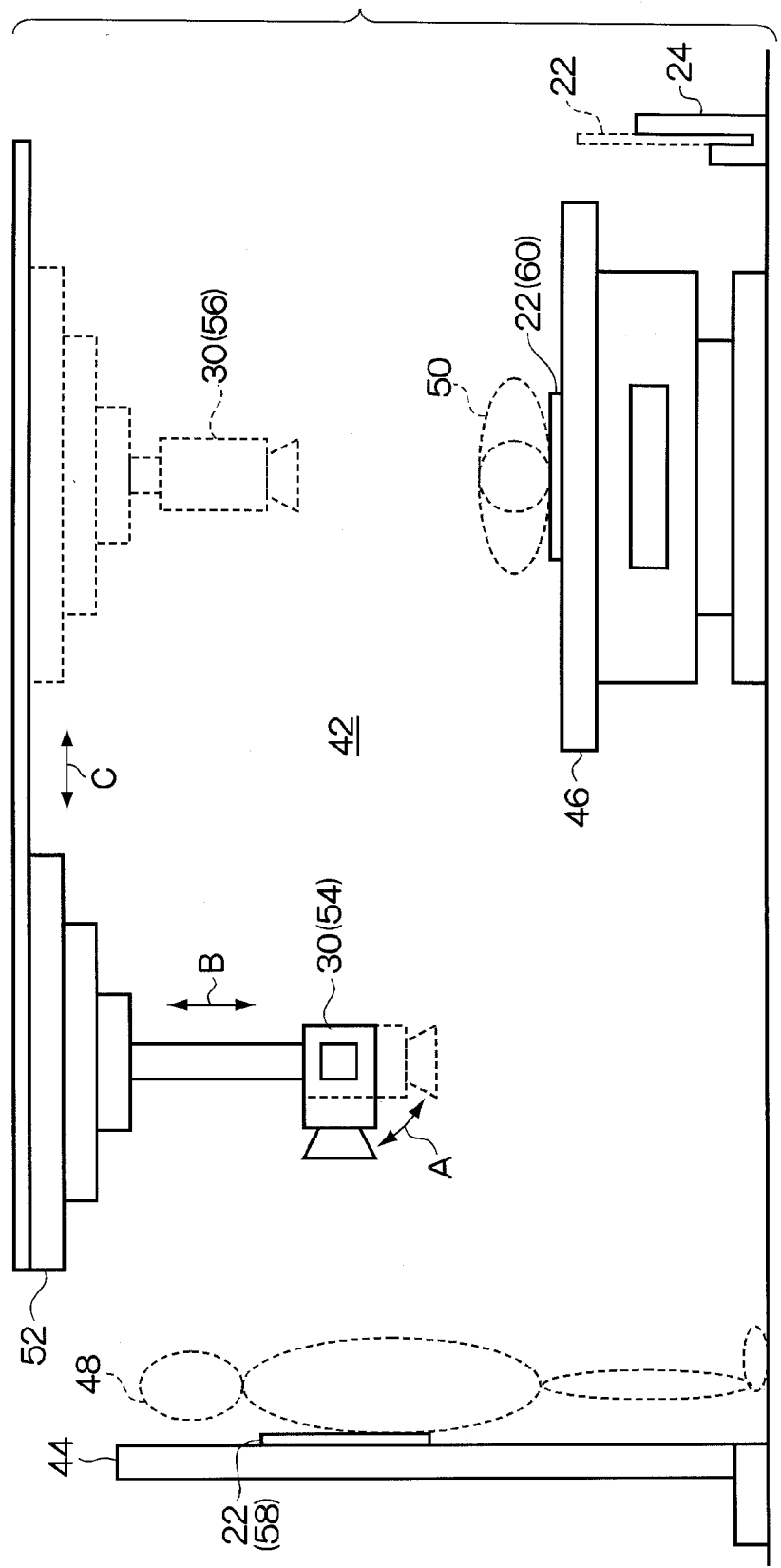
FIG. 3 is a schematic view illustrating an example of a layout of a radiation generating apparatus or an electronic cassette in a imaging room.

As shown in FIG. 3, in the radiographic image capturing room 42 where the radiation source 30 is installed, a rack 44 which supports the electronic cassette 22 at the time of radiographic imaging in an erect position and a bed 46 on which a patient lies at the time of radiographic imaging in a lying position are disposed. The front space of the rack 44 is an imaging position 48 of the patient at the time of radiographic imaging in the erect position, and the upper space of the bed 46 is an imaging position 50 of the patient at the time of radiographic imaging in the lying position. In the radiographic image capturing room 42, in order to perform the radiographic imaging in the erect position as well as in the lying position with the radiation from a single radiation source 30, disposed is a movement supporting mechanism 52 which supports the radiation source 30 to be rotated about a horizontal axis (direction of arrow A in FIG. 3), to be moved in the vertical direction (direction of arrow B in FIG. 3), and to be moved in the horizontal direction (direction of arrow C in FIG. 3).

A radiation source moving unit 38 includes a driving source (not shown) for rotating the radiation source 30 about the horizontal axis, a driving source (not shown) for moving the radiation source 30 in the vertical direction, and a driving source (not shown) for moving the radiation source 30 in the horizontal direction. The imaging condition information received from the console 26 includes information indicating whether the imaging posture is in the erect position or in the lying position. If the imaging posture indicated by the received imaging condition information is in the erect position, the radiation source control unit 32 controls the radiation source moving unit 38 so that the radiation source 30 is disposed at the erect-position imaging position 54 (the position where the patient in the imaging position 48 is irradiated from the side of the patient with the emitted radiation). If the imaging posture indicated by the received imaging condition information is in the lying position, the radiation source control unit 32 controls the radiation source moving unit 38 so that the radiation source 30 is disposed at the lying-position imaging position 56 (the position where the patient in the imaging position 50 is irradiated from the upper position of the patient with the emitted radiation).

If the imaging posture is in the erect position, the radiological technologist moves the electronic cassette 22 to the position 58 supported by the rack 44. If the imaging posture is in the lying position, the radiological technologist moves and disposes the electronic cassette 22 to the position 60 on the bed 46. Details of the electronic cassette 22 will be described later.

As shown in FIG. 2, the cradle 24 includes a cradle control unit 62 that controls the entire operations of the cradle 24. The cradle control unit 62 is connected to a power supplying unit 63 and a wireless communication unit 64. As shown in FIG. 3, a casing of the cradle 24 has a recessed shape so that the electronic cassette 22 may be inserted to a recessed portion. The power supplying unit 63 supplies a power to the battery 116 of the electronic cassette 22 in the state that the electronic cassette 22 is inserted into the recessed portion of the casing of the cradle 24, so that the battery 116 is charged. A wireless antenna 65 is connected to the wireless communication unit 64. The wireless communication unit 64 wirelessly communicates with other components of the same radiographic imaging system 18 through the wireless antenna 65 via the wireless network 28.

In the exemplary embodiment, as described later, the data of the radiographic image generated by the electronic cassette 22 in the radiographic imaging is directly transmitted from the electronic cassette 22 through the wireless network 28 to the console 26, but not limited thereto. In the state that the electronic cassette 22 is inserted to the recessed portion of the casing of the cradle 24, a communication function using, for example, a laser beam may be provided to the electronic cassette 22 and the cradle 24, and the cradle 24 may be configured so that the data of the radiographic image is received from the electronic cassette 22 in the above state by the aforementioned communication function and temporarily stored in a memory or the like and the temporarily stored data of the radiographic image may be transmitted to the console 26 at a suitable timing.

The console 26 includes a system control unit 66 that is configured with a PC or the like. The system control unit 66 includes a CPU 66A, a memory 66B including a ROM and a RAM, a nonvolatile storage unit 66C that is configured with a hard disk drive (HDD), a flash memory, or the like. A display 67 such as a liquid crystal display (LCD), an input unit 68 such as a keyboard or a mouse, a communication interface (I/F) unit 69 for communicating with the hospital intranet 16 (refer to FIG. 1), and a wireless communication unit 59 are connected to the system control unit 66. A wireless antenna 61 is connected to the wireless communication unit 59. The wireless communication unit 59 wirelessly communicates with other components of the same radiographic imaging system 18 through the wireless antenna 61 via the wireless network 28.

Figure 4:
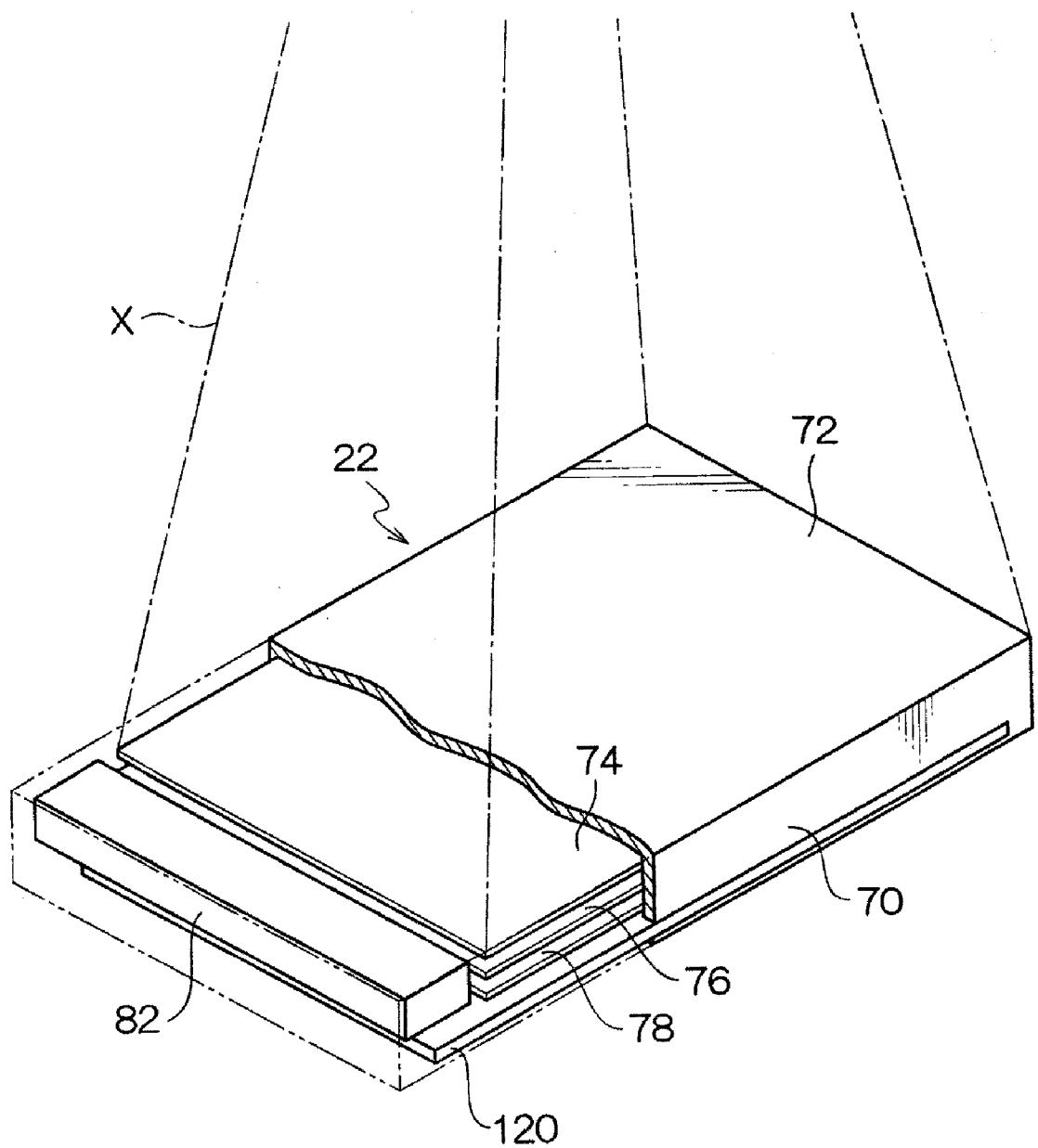
FIG. 4 is a perspective view illustrating an internal structure of an electronic cassette according to an exemplary embodiment.

Next, the electronic cassette 22 according to the invention is described. As shown in FIG. 4, the electronic cassette 22 is covered with a flat (flat box shape) casing 70 which is made of a material that can be penetrated by a radiation (denoted by reference numeral "X" in FIG. 4) and which has a thickness. Within the casing 70, a grid 74 for removing a scattered ray of the radiation generated due to the penetration in the object to be imaged, a radiation detector (radiation detecting panel) 76 for detecting the radiation, and a lead sheet 78 are disposed sequentially from a side of a to-be-irradiated surface 72 on which the radiation is irradiated in the casing 70. The to-be-irradiated surface 72 of the casing 70 may be configured with the grid 74. In addition, a case 82 for receiving various circuits described later is disposed at the one end side of the inner portion of the casing 70. In order to prevent the various circuits received in the case 82 from being damaged due to the irradiation of the radiation, it is preferable that the lead sheet 78 or the like is disposed at the side of the to-be-irradiated surface 72 of the case 82. The radiation detector 76 together with a signal processing unit 102 described later corresponds to an image output unit according to the invention.

In the exemplary embodiment, within the casing 70 of the electronic cassette 22, a receiving space (hereinafter, referred to as a receiving portion 122, see FIG. 5B) for receiving a display unit 120 including a display device capable of displaying an image is disposed at a rear side of a lead sheet 78 as seen from the to-be-irradiated surface 72. As shown in FIGS. 5A, 5B, and 6A to 6C, the display unit 120 according to the exemplary embodiment has an overall flat rectangular parallelepiped shape, and the receiving portion 122 has a shape and size capable of receiving the entire portion of the display unit 120. The display unit 120 is received in the receiving portion 122 in the direction that the display surface faces upwards, in the state that one of the two plane facing each other with a rectangular shape is used as the display surface where the display region for displaying an image by the display device is disposed and the casing 70 of the electronic cassette 22 is disposed so that the to-be-irradiated surface 72 faces upwards. In addition, in the exemplary embodiment, since the display region disposed in the display surface has a rectangular shape, LCD is suitable for the display device, but other display devices may be used.

As shown in FIGS. 5A, 5B, and 6A to 6C, on the casing 70 of the electronic cassette 22, a handle 124 for holding the electronic cassette 22 (casing 70) at the time of moving the electronic cassette 22 is provided to a side abutting the to-be-irradiated surface 72. A flat rectangular opening 126 capable of passing the display unit 120 is disposed at a specific side where the handle 124 is disposed on the casing 70. The receiving portion 122 is connected to an outer portion of the casing 70 through the opening, and the display unit 120 is inserted into the receiving portion 122. An expanding manipulation for slidingly moving the display unit 120 in a direction (direction of arrow D in FIG. 6B) of ejecting the display unit 120 from the receiving portion 122 of the casing 70 is performed, so that the display surface is expanded outside the casing 70 where the handle is provided, and the display unit 120 becomes in the state that the most portion of the display unit 120 is exposed outside the casing 70 (the state shown in FIG. 6C). Hereinafter, the position of the display unit 120 in this state is referred to as a displayable position. On the other hand, a receiving manipulation for slidingly moving the display unit 120 in a direction (direction of arrow E in FIG. 6B) of inserting the display unit 120 into the receiving portion 122 of the casing 70 from the state that the display unit 120 is in the displayable position is performed, so that the display unit 120 becomes in the state that the entire portion of the display unit 120 is received in the receiving portion 122 (the state shown in FIGS. 5A and 6A). Hereinafter, the position of the display unit 120 in this state is referred to as a receiving position.

Figure 5A:
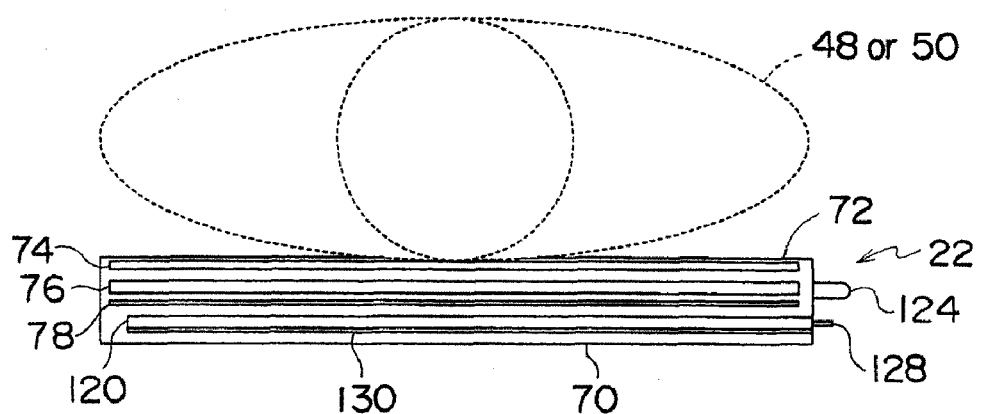
FIG. 5A is a side view illustrating an internal structure of an electronic cassette.
Figure 6A:
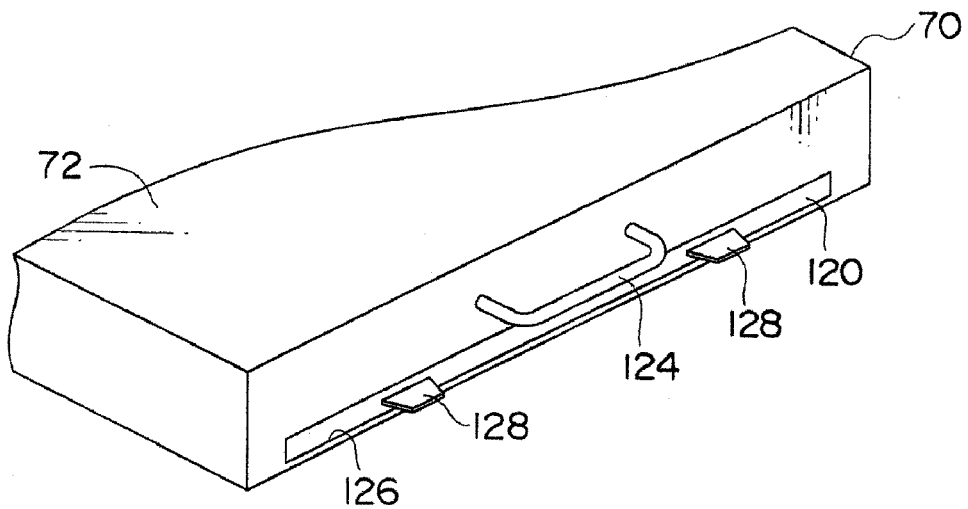
FIG. 6A is a perspective view illustrating receiving/expanding of a display unit of an electronic cassette.
Figure 6B:
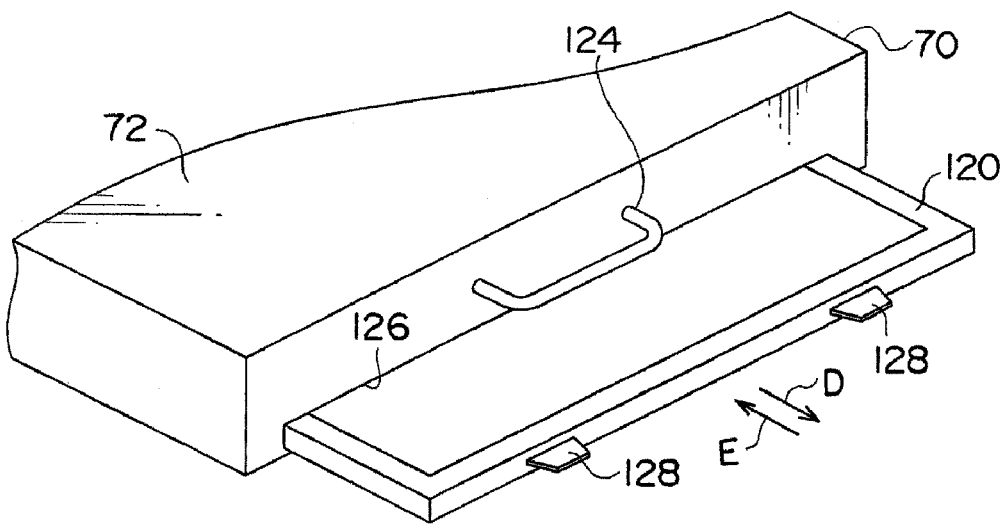
FIG. 6B is a perspective view illustrating receiving/expanding of a display unit of an electronic cassette.

A pair of grips 128 are provided to the side surface of the display unit 120, which closes the opening 126 in the state that the entire portion of the display unit 120 is received in the receiving portion 122 (the state shown in FIGS. 5A and 6A). If the user (radiological technologist) grasps the pair of grips 128 performs the aforementioned receiving manipulation or expanding manipulation, the display unit 120 is slidingly moved to the aforementioned receiving position or displayable position. In addition, a stopper (not shown) for limiting the sliding movement of the display unit 120 to the displayable position in the direction of ejecting the display unit 120 from the receiving portion 122 is provided in the vicinity of the end portion opposite to the side where the grips 128 of the display unit 120 are provided. Due to the stopper, separation of the entire portion of the display unit 120 from the receiving portion 122 (that is, the separation of the display unit 120 from the casing 70 of the electronic cassette 22) may be prevented. In this manner, the display unit 120 is provided to the casing 70 so that the display surface thereof may be received.

Figure 5B:
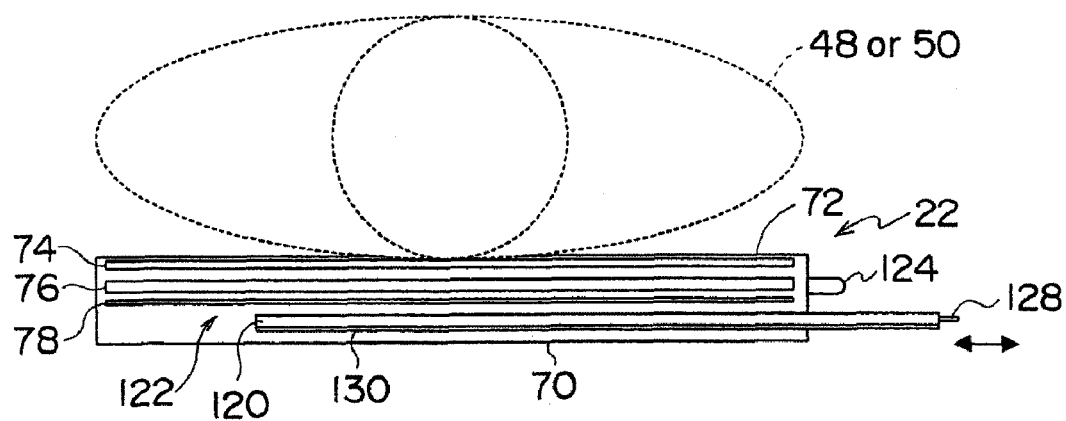
FIG. 5B is a side view illustrating an internal structure of an electronic cassette.

As shown in FIGS. 5A and 5B, a lead sheet 130 is attached to the rear surface (that is, the surface opposite to the to-be-irradiated surface 72) of the display unit 120. Since the aforementioned lead sheet 78 is provided, the back scattering of the radiation may be absorbed and reduced, and the deterioration in the radiation in the state that the display unit 120 is received into the receiving portion 122 may be suppressed. Furthermore, the lead sheet 130 is disposed in order to supplement the absorption and reduction of the back scattering of the radiation by the lead sheet 78. Preferably, a lead sheet configured with a lead having a thickness of 0.5 mm or more may be used as the lead sheet 78, and a lead sheet configured with a lead having a thickness of 0.2 mm or more may be used as the lead sheet 130.

The radiation detector 76 of the electronic cassette 22 is configured by laminating a photoelectric conversion layer of absorbing a radiation and converting the radiation to charges on the TFT active matrix substrate 86 shown in FIG. 2. The photoelectric conversion layer is made of, for example, an amorphous a-Se (amorphous selenium) containing selenium as a main ingredient (for example, a containing ratio of 50% or more). When the radiation is irradiated, the photoelectric conversion layer converts the irradiated radiation to charges by generating charges (electron-hole pairs) having a charge amount corresponding to the amount of irradiated radiation in an inner portion thereof. The radiation detector 76 is not limited to the aforementioned configuration where the radiation is directly converted to the charges by using a radiation-charge conversion material such as the amorphous selenium. Alternatively, the radiation detector 76 may employ a configuration where the radiation is indirectly converted to the charges by performing a radiation-photon conversion by using a fluorescent material such as gadolinium oxysulfide (GOS) or cesium iodide (CsI) and performing a photon-charge conversion by using a photoelectric conversion device such as a photodiode.

On the TFT active matrix substrate 86, plural pixel units 94 (FIG. 1 schematically shows the photoelectric conversion layer corresponding to each pixel unit 94 as the photoelectric conversion portion 92) including storage capacitors 88 which store the charges generated in the photoelectric conversion layers and TFTs 90 which are used for reading out the charges stored in the storage capacitors 88 are disposed in a matrix. The charges that are generated in the photoelectric conversion layers due to the irradiation of the radiation on the electronic cassette 22 are stored in the storage capacitors 88 of the pixel units 94. Accordingly, the image information contained in the radiation irradiated on the electronic cassette 22 is converted to the charge information to be stored in the radiation detector 76.

In addition, in the TFT active matrix substrate 86, disposed are plural gate lines 96 which are disposed to extend in a predetermined direction (row direction) and used for turning on and off the TFTs 90 of the pixel units 94 and plural data lines 98 which are disposed to extend in a direction (column direction) perpendicular to the gate lines 96 and used for reading out the stored charges from the storage capacitors 88 through the turned-on TFTs 90. Each of the gate lines 96 is connected to a gate line driver 100, and each of the data lines 98 is connected to a signal processing unit 102. When the charges are stored in the storage capacitors 88 of the pixel units 94, the TFTs 90 of the pixel units 94 are sequentially turned on in units of row by a signal applied from the gate line driver 100 through the gate lines 96. The charges stored in the storage capacitors 88 of the pixel unit 94 of which TFTs 90 are turned on are transmitted as a charge signal through the data lines 98 to be input to the signal processing unit 102. Accordingly, charges stored in the storage capacitor 88 of each pixel unit 94 are sequentially read out in units of row.

Although not shown, the signal processing unit 102 includes amplifiers and sample hold circuits that are provided to each of the data lines 98. The charge signal transmitted through each data line 98 is amplified by the amplifier, and after that, stored in the sample hold circuit. A multiplexer and an A/D converter are sequentially connected to an output side of the sample hold circuit. The charge signal stored in each sample hold circuit is sequentially (serially) input to the multiplexer to be converted to a digital image data in the A/D converter. The signal processing unit 102 is connected to an image memory 104. The image data output from an A/D converter of the signal processing unit is sequentially stored in the image memory 104. The image memory 104 has a storage capacity that may store an image data corresponding to a plurality of frames. At every time of capturing the radiographic image, the image data obtained by the imaging are sequentially stored in the image memory 104. The image memory 104 corresponds to a first storage unit according to the invention.

The image memory 104 is connected to a cassette control unit 106. The cassette control unit 106 that is configured with a micro-computer or the like includes a CPU 106A, a memory 106B including a ROM and a RAM, and a nonvolatile storage unit 106C that is configured with an HDD, a flash memory, or the like. An information display program for executing an information displaying process described later is stored in the storage unit 106C. Although not shown, the cassette control unit 106 is connected to the gate line driver 100 and the signal processing unit 102 described above, to control reading out charges from each pixel unit 94 by the gate line driver 100 and the signal processing unit 102. In addition, the display unit 120, the input unit 108, the ejecting sensor 110, and the wireless communication unit 112 are connected to the cassette control unit 106.

The cassette control unit 106 that performs an information displaying process described later displays on the display unit 120 information such as radiographic image indicated by an image data stored in the image memory 104. The cassette control unit 106 corresponds to a display control unit according to the invention. In the exemplary embodiment, the input unit 108 is configured with a touch panel disposed on a display surface of the display unit 120. A user performs manipulations on the input unit 108 (touch panel) to input information corresponding to the manipulations to the cassette control unit 106. The ejecting sensor 110 is a sensor that is disposed to the receiving portion 122 to detect whether or not the display unit 120 is ejected from the receiving portion 122. A result of the detection of the ejecting sensor 110 is also input to the cassette control unit 106. A wireless antenna 114 is connected to the wireless communication unit 112. The wireless communication unit 112 wirelessly communicates with other components of the same radiographic imaging system 18 through the wireless antenna 114 via the wireless network 28. The wireless communication with other components by the wireless communication unit 112 may be an optical wireless communication using infra red or the like instead of a typical wireless communication using an electric wave.

The electronic cassette 22 includes a battery 116. The aforementioned circuits (the gate line driver 100, the signal processing unit 102, the image memory 104, the cassette control unit 106, the display unit 120, the input unit 108, the wireless communication unit 112, and the like) are operated by a power supplied from the battery 116. In the exemplary embodiment, a secondary battery that is charged by a power supplied from the power supplying unit 63 of the cradle 24 is used as the battery 116, but not limited thereto. Alternatively, a primary battery may be used as the battery 116. Instead of the battery 116, a power supply unit which is always connected to a commercial power source to rectify and transform a power supplied from the commercial power source and to supply a power to various circuits may be provided.

Next, operations of the exemplary embodiment are described. In the exemplary embodiment, although the electronic cassette 22 are moved and positioned at the position 58 or the position 60 in the radiographic image imaging room 42 according to the imaging posture for the radiographic image, in the electronic cassette 22 according to the exemplary embodiment, the display unit 120 may be received in the receiving portion 122 in the casing 70. Therefore, in a case where the electronic cassette 22 is to be moved and positioned at the position 58 or the position 60 or in a case where the electronic cassette 22 is carried out from the radiographic image imaging room 42 so as to be used for radiographic imaging in another imaging room or surgery room, or in a vehicle mounted with the radiographic imaging apparatus, the aforementioned receiving manipulation is performed to receive the display unit 120 in the receiving portion 122 in the casing 70, so that it is possible to prevent the display unit 120 from interfering with the movement of the electronic cassette 22.

In addition, in the electronic cassette 22 according to the exemplary embodiment, the display surface of the display unit 120 may be expanded outside the casing 70 by performing the expanding manipulation for slidingly moving the display unit 120 in the direction of ejecting the display unit 120 from the receiving portion 122 of the casing 70. Therefore, the expanding manipulation for expanding the display surface outside the casing 70 may be easily performed, so that a good workability may be obtained. In addition, in case of performing the aforementioned expanding manipulation, although the display surface of the display unit 120 is expanded in a space other than the side surface where the handle 124 of the casing 70 is provided, the movement or position adjustment of the electronic cassette 22 is performed in the state that the handle 124 is grasped. Therefore, in general, since other components are not disposed in the space, it is possible to prevent other components from interfering with the expansion of the display surface of the display unit 120.

Figure 6C:
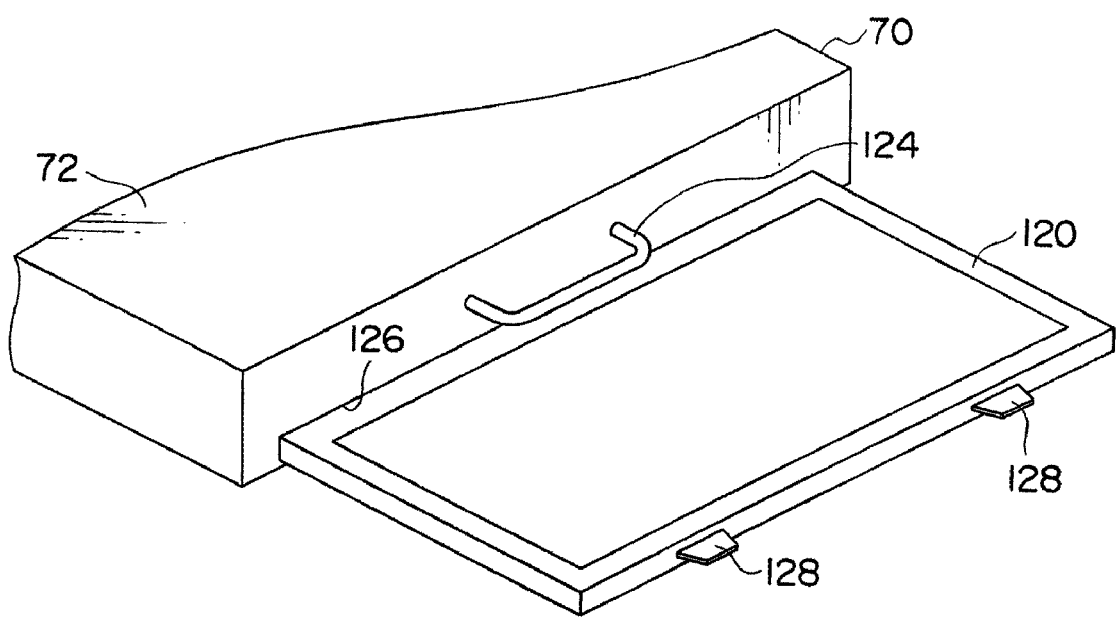
FIG. 6C is a perspective view illustrating receiving/expanding of a display unit of an electronic cassette.

In addition, a stopper (not shown) for limiting the ejection of the display unit 120 from the receiving portion 122 to the displayable position shown in FIG. 6C is provided to the casing 70 so that the display unit 120 is not separated from the casing 70. Therefore, even in a case where the electronic cassette 22 is moved and positioned at a desired position and the display surface of the display unit 120 is expanded outside the casing 70 by ejecting the display unit 120 from the receiving portion 122 to the displayable position through the aforementioned expanding manipulation, the display unit 120 is supported by the casing 70 to maintain a positional relationship with respect to the casing 70 shown in FIG. 6C. Accordingly, any supporting mechanism for supporting the display unit 120 is unnecessary. In addition, due to the display unit 120, deterioration in workability or portability of the electronic cassette 22 may be prevented. In addition, even in a case where a patient as an object to be imaged is located at a position indicated by the broken lines FIGS. 5A and 5B with respect to the casing 70 of the electronic cassette 22, by expanding the display surface of the display unit 120 outside the casing 70, the state that the display surface of the display unit 120 is in contact with the patient's body or the state that the display surface of the display unit 120 is shielded by the patent's body may be prevented. Accordingly, the user may surely have a view of the information of the radiographic image and the like displayed by the display unit 120.

Next, the radiographic imaging in the RIS 10 is described. When a surgeon or a radiological technologist requests for capturing a radiographic image through the terminal 12, information (for example, patient ID) for identifying a to-be-imaged patient, information of imaged portion and imaging posture, and the like are input to the terminal 12. In a case where a patient tag recorded with the patient ID is carried by (or attached to) the patient, the inputting of the information for identifying the patient is performed by a reader device (connected to the terminal 12) reading out the patient ID recorded in the patient tag carried by the to-be-imaged patient. The request for capturing the radiographic image that is performed by the terminal 12, together with the information input to the terminal 12, is transmitted to the RIS server 14 and received by the RIS server 14.

When the RIS server 14 receives the request for capturing the radiographic image from the terminal 12, the RIS server 14 selects one radiographic imaging system 18 that is to perform capturing the radiographic image corresponding to the received request of imaging with reference to a previously recorded schedule of capturing radiographic images in a plurality of the radiographic imaging systems 18 and determines a date at which the selected radiographic imaging system 18 is to perform capturing the radiographic image. In addition, the RIS server 14 reads out needed information such as attribute information of the patient from the RIS database and transmits the read-out information, the determined imaging date, and the like together with the information received from the terminal 12 to the console 26 of the selected radiographic imaging system 18.

Every time when the information is received from the RIS server 14, the console 26 stores the received information in the storage unit 66C. In response to a command of the user (radiological technologist), the console 26 displays on the display 67 the information stored in the storage unit 66C as the schedule of capturing the radiographic image and details of imaging (for example, a name, imaged portion, and imaging posture of a to-be-imaged patient and standard driving conditions of a radiation tube defined in one-to-one correspondence with the imaged portion, and the like). When the capturing of the radiographic image is to be performed, the console 26 transmits to the radiation generating apparatus 20 the imaging condition information indicating the imaging conditions in the to-be-performed radiographic imaging. The radiation source control unit 32 of the radiation generating apparatus 20 controls the radiation source moving unit 38 so that the radiation source 30 is positioned at the position corresponding to the imaging posture indicated by the received imaging condition information.

When the capturing of the radiographic image is to be performed, the user (radiological technologist) checks the imaged portion, the imaging posture, the driving conditions of the radiation tube, and the like from the console 26 to move and position the electronic cassette 22 to the position (the position 58 or the position 60) according to the imaging posture in the radiographic image imaging room 42. The user identifies the name of the to-be-imaged patient and positions the patient at the position (the position 48 or the position 50) according to the imaging posture. If needed, the user performs a series of preparing operations such as fine position adjusting of the radiation source 30. When a series of the preparing operations are completed, the user turns on the exposure switch 34.

An amount of radiation according to the driving conditions of the radiation tube included in the imaging condition information that the radiation generating apparatus 20 receives from the console 26 is generated and emitted from the radiation source 30. The radiation emitted from the radiation source 30 penetrates the patient to be irradiated on the to-be-irradiated surface 72 of the electronic cassette 22. In the electronic cassette 22, the radiation irradiated on the to-be-irradiated surface 72 is converted to charges to be stored by the radiation detector 76. After that, the stored charges are read out through the gate line driver 100 and the signal processing unit 102 to be converted to the data of the radiographic image and to be stored in the image memory 104.

The data of the radiographic image stored in the image memory 104 is transmitted from the electronic cassette 22 through the wireless network 28 to the console 26 to be stored in the storage unit 66C of the console 26. The data of the radiographic image stored in the storage unit 66C is displayed on the display 67 so as to check the captured radiographic image. In addition, the data of the radiographic image is transferred to the RIS server 14 to be stored in the RIS database. As a result, the captured radiographic image is displayed on a display of the terminal 12, so that the surgeon may read out the radiographic image and perform diagnosis.

In the radiographic imaging, if the patient moves, blur of the object to be imaged may occur in the radiographic image. In this case, the imaging needs to be performed again. Therefore, the user needs to check whether or not the blur of the object to be imaged in the captured radiographic image occur. In addition, in a case where there is a previously-captured radiographic image for the same portion of the same patient, the user needs to designate the imaging range (positioning) of the current imaging to be equal to be the imaging range of the previously-captured radiographic image, by referring to the previously-captured radiographic image so as for a surgeon to facilitate the reading of the radiographic image. In addition, although the imaging posture is designated to be the erect position, if the patient arriving in the radiographic imaging room 42 is in the state the erect position imaging is difficult (for example, if a patient's leg is hurt), changing of the imaging posture may be preferable. Moreover, the driving conditions of the radiation tube may be needed to be changed.

The checking of the captured radiographic image, the referring to the previously-captured radiographic image, and the changing of the imaging posture or the driving conditions of the radiation tube may be performed by manipulating the console 26. However, since the console 26 is generally installed outside the radiographic imaging room 42 (for example, another room adjacent to the radiographic imaging room 42), in the above case, the user needs to go and come between the radiographic imaging room 42 and the site installed with the console 26 during the preparing operations or every time of the imaging. Accordingly, there is a problem in that the work efficiency is lowered. In addition, since the adjusting of the imaging range (positioning) with reference to the previously-captured radiographic image may not be performed, there is a problem in that the accuracy of the adjusting of the imaging range is not satisfactory.

In order to solve the problems, the display unit 120 is provided to the electronic cassette 22 according to the exemplary embodiment. In a case where the checking of the captured radiographic image, the referring to the previously-captured radiographic image, and the changing of the imaging posture or the driving conditions of the radiation tube is performed or likely to be performed, the user grasps the grip 128 and ejects the display unit 120 from the casing 70 (the receiving portion 122) of the electronic cassette 22 to perform the manipulation of expanding the display surface of the display unit 120 outside the casing 70. When the manipulation is performed, the ejection of the display unit 120 is detected by the ejecting sensor 110. Due to the detection, an information displaying process shown in FIG. 7 is triggered by the cassette control unit 106 of the electronic cassette 22.

In the information displaying process, firstly in a step 300, information requesting for transmitting various information (for example, a patient ID, name, imaged portion, radiographic imaging history, and imaging posture of a to-be-imaged patient, a tube voltage and tube current of a radiation tube, and the like; hereinafter, referred to as RIS information) that is to be displayed by the display unit 120 is transmitted through the wireless communication unit 112 to the console 26, so that the transmission of the RIS information is requested to the console 26. In next step 302, it is determined whether or not information is received from another apparatus. If a result of the determination is negative, the process proceeds to a step 304, in which it is determined whether or not information is input through the input unit 108 configured with a touch panel. If a result of the determination is negative, the process proceeds to a step 306, in which it is determined whether or not the receiving of the display unit 120 into the receiving portion 122 is detected by the ejecting sensor 110. If a result of the determination is negative, the process returns to the step 302, and the steps 302 to 306 are repeated until any of the results of the above determinations are affirmative.

When receiving the information requesting for transmitting the RIS information from the electronic cassette 22, the console 26 reads out the information associated with the current imaging from the storage unit 66C and edits the read-out information as the RIS information to transmit the RIS information through the wireless communication unit 59 to the electronic cassette 22. When the RIS information is received through the wireless communication unit 112 of the electronic cassette 22 and input to the cassette control unit 106, the determination of the step 302 becomes affirmative, and thus, the process proceeds to a step 308. In the step 308, the process is branched according to the classification of the received information. If the received information is the RIS information received from the console 26, the process proceeds from the step 308 to a step 310, in which the RIS information received from the console 26 is stored in the memory 106B.

Figures 8A, 8B:
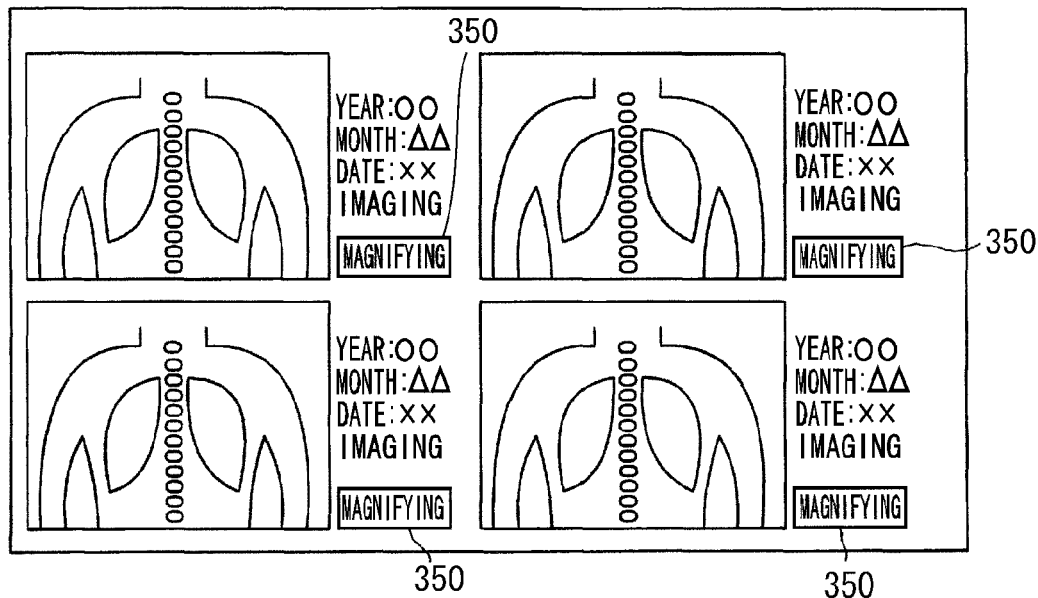
FIG. 8A is an image view illustrating an example of information displayed on a display surface of a display unit.
FIG. 8B is an image view illustrating an example of information displayed on a display surface of a display unit.

In next step 312, the RIS information received from the console 26 is displayed on the display surface of the display unit 120 as an RIS information displaying/correcting window. As shown in FIG. 8A, the RIS information displaying/correcting window is a window that displays details of the received RIS information (for example, a patient ID, name, radiographic imaging history, imaged portion, and imaging posture of a to-be-imaged patient, a tube voltage and tube current of a radiation tube, and the like) and through which a command of correcting some items (for example, the imaging posture, the tube voltage and tube current of the radiation tube, and the like) may be input by the user (radiological technologist). Since the window is displayed on the display surface of the display unit 120, the details of the to-be-performed radiographic imaging may be checked.

Since the patient ID or name is displayed on the window, it may be surely checked in the radiographic imaging room 42 whether there is an identification error for the to-be-imaged patient, by identifying, for example, the name of the patient and comparing the identified name with the name displayed on the window. In addition, since the command of correcting the imaging posture, the tube voltage and tube current of the radiation tube, and the like are displayed on the widow so as for the user to input the command, the user checks the items. In a case where the correcting is determined to be needed, the user input the command of correcting through the input unit 108 configured with a touch panel, so that the imaging posture, the tube voltage and tube current of the radiation tube, and the like may be changed without coming and going between the radiographic imaging room 42 and the site installed with the console 26.

In next step 314, request information of requesting for the data of the previously-captured relevant radiographic image is generated. When the information is generated, it is determined whether or not the same portion of the patient on which the current radiographic imaging is to be performed was previously captured, with reference to the radiographic imaging history included in the received RIS information. In a case where the same portion of the patient on which the current radiographic imaging is to be performed was previously captured, the patient ID and the imaged portion are extracted from the received RIS information, and the extracted patient ID and imaged portion are added as the previous image search condition to the request information to be transmitted to the console 26. Accordingly, the transferring of the data of the previously-captured radiographic image of which patient and imaged portion are the same as those of the current imaging is requested to the console 26.

On the other hand, in a case where the same portion of the patient on which the current radiographic imaging is to be performed was not previously captured, only the imaged portion is extracted from the received RIS information, and the extracted imaged portion is added as the previous image search condition to the request information to be transmitted to the console 26. Accordingly, the transferring of the data of the previously-captured radiographic image of which imaged portion is the same as that of the current imaging is requested to the console 26.

When receiving the request information from the electronic cassette 22, the console 26 transfers the received request information to the RIS server 14, so that the data of the previously-captured relevant radiographic image is requested to the RIS server 14. When receiving the request information from the console 26, the RIS server 14 searches the RIS database by using the previous image search condition (patient ID and imaged portion, or imaged portion) added to the received request information as a key. The RIS server 14 reads out the data of the radiographic image from the RIS database and transmits the data to the console 26 that requests for the data. Accordingly, in a case where the patient ID and the imaged portion are designated as the search condition, the data of the radiographic image obtained by previously imaging the same portion of the patient on which the current radiographic imaging is to be performed is transmitted from the RIS server 14 to the console 26. On the other hand, in a case where only the imaged portion is designated as the search condition, the data of the radiographic image obtained by previously imaging the same portion of a patient different from the patient on which the current radiographic imaging is to be performed is transmitted from the RIS server 14 to the console 26.

Particularly, in the case where only the imaged portion is designated as the previous image search condition, a plurality of data are likely to be extracted as the data of the radiographic images. Therefore, in the exemplary embodiment, the upper limit of the number of data of the radiographic images that are read out from the RIS database to be transmitted is set. In a case where the number of data of the radiographic image corresponding to the set search condition is more than the upper limit, for example, the RIS server 14 reads out the data of the radiographic images of which number is equal to the upper limit in the descending order (newest-first order) of imaging dates and transmits the data. When receiving the data of the radiographic image requested by the electronic cassette 22 from the RIS server 14, the console 26 transmits the received data of the radiographic image to the requesting electronic cassette 22. The RIS server 14 and the console 26 correspond to a radiographic image management apparatus according to the invention.

In the exemplary embodiment, in the case where the same portion of the patient on which the current radiographic imaging is to be performed was not previously captured, the previously-captured radiographic image is searched and extracted by using only the "the same imaged portion" as the condition, but not limited thereto. For example, the searching and extracting of the radiographic image may be performed by using, for example, "the same gender", "the same age", or "the same physical feature (height, weight, or the like)" as the additional condition.

Figure 8C:
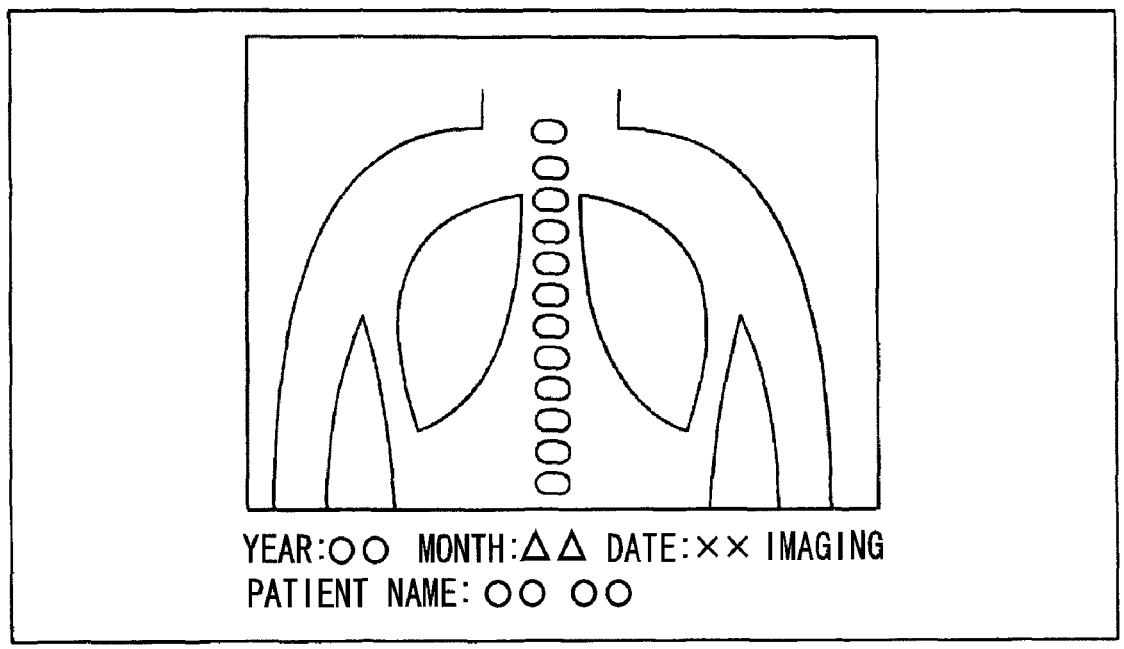
FIG. 8C is an image view illustrating an example of information displayed on a display surface of a display unit.

If the data of the radiographic image is received by the electronic cassette 22, a result of the determination of the step 302 of the information displaying process (refer to FIG. 7) becomes affirmative, so that the process proceeds to the step 308. If the received information is the data of the radiographic image received from the console 26, the process is branched from the step 308 to a step 315. In the step 315, the data of the radiographic image received from the console 26 is stored in the memory 106B. In next step 316, it is determined whether or not plural the data of the radiographic images are received from the console 26. If a result of the determination is negative, the process proceeds to the step 317, in which one radiographic image in the data received from the console 26 is displayed on the display unit 120 as shown in FIG. 8C. The process returns to the step 302, and the steps 302 to 306 are repeated.

In this case, user may grasp the imaging range of the previous imaging for the same imaged portion by referring to the radiographic image displayed on the display unit 120. The user may adjust the imaging range of the current imaging to be as equal to the grasped imaging range as possible, without coming and going between the radiographic image imaging room 42 and the site installed with the console 26. In addition, in this case, the user may more accurately adjust the imaging range of the current imaging, in comparison with a case where the previously-captured radiographic image is displayed on the display 67 of the console 26 installed outside the radiographic imaging room 42. In addition, in a case where the radiographic image displayed on the display unit 120 is a radiographic image obtained from the previous imaging on the same imaged portion of the patient on which the current radiographic imaging is to be performed, when the radiographic image obtained from the current imaging is referred by a surgeon, the associated radiographic image is highly likely to be referred at the same time by the surgeon. As described above, the imaging range of the current imaging may be adjusted to be equal to the imaging range of the radiographic image displayed on the display unit 120. Therefore, the accuracy of the reading of the radiographic image and the diagnosis performed by the surgeon may be further improved.

On the other hand, if a result of the determination of the step 316 is affirmative, the process proceeds to the step 318, in which the radiographic images in the data received from the console 26 are reduced and displayed in a table manner on the display unit 120, as shown in FIG. 8B. The process returns to the step 302, and the steps 302 to 306 are repeated. In a case where a plurality of the previously-captured radiographic images are reduced and displayed in a table manner, as shown in FIG. 8B, buttons 350 for commanding of magnifying and displaying of the radiographic images are provided to the radiographic images. When the user is to magnify and display a specific radiographic image among the plurality of the reduced radiographic images displayed in the table manner and to check the imaging range thereof, the user performs a manipulation of selecting the button 350 provided to the to-be-checked specific radiographic image.

When the manipulation is performed, a result of the determination of the step 304 becomes affirmative, so that it is determined whether or not the information input in the step 326 is information of commanding the correcting of the imaging conditions. In this case, a result of the determination becomes negative, and the process proceeds to the step 330, in which it is determined whether or not the input information is information of selecting any one radiographic image among the plurality of the radiographic image (previously-captured radiographic images) displayed in the table manner on the display unit 120. In this case, a result of the determination becomes affirmative, the process proceeds to the step 332, in which the selected one radiographic image is more magnified and displayed (than the images in the table-displayed window in FIG. 8B) on the display surface of the display unit 120, as shown in FIG. 8C. Accordingly, as described above, the imaging range may be adjusted with a high accuracy by referring to the radiographic image displayed on the display unit 120.

It is determined whether or not the input information is information of commanding the magnifying and displaying of the image in next step 334. In this case, a result of the determination becomes negative, the process proceeds to the step 338. In the step 338, it is determined whether or not the input information is information indicating the ending of checking the image. In this case, a result of the determination becomes negative, and the process returns to the step 302, and the steps 302 to 306 are repeated.

In addition, as described above and later, in the state that the aforementioned RIS information displaying/correcting window is displayed on the display unit 120, the input unit 108 configured with a touch panel is manipulated by the user. In a case where the information of commanding the correcting of the imaging conditions such as the imaging posture or the tube voltage and tube current of the radiation tube is input, a result of the determination of the step 304 becomes affirmative, and a result of the determination of the step 326 also becomes affirmative. Therefore, the process proceeds to the step 328, in which the details of the item among the RIS information stored in the memory 106B are corrected according to the input information of commanding the correcting. The corrected RIS information is transmitted to the console 26. In this case, results of the determination of the steps 330, 334, and 338 become negative. The process returns to the step 302, and the steps 302 to 306 are repeated.

In a case where the RIS information corrected according to a user's command is received from the electronic cassette 22, the console 26 edits the RIS information received from the electronic cassette 22 as the imaging condition information to transmit the information to the radiation generating apparatus 20. At the same time, the console 26 corrects the information corresponding to the received RIS information among the information stored in the storage unit 66C, based on the received RIS information. If the item corrected according to the user's command is an item associated with the driving conditions of the radiation tube such as the tube voltage or the tube current, the radiation tube is driven with the driving conditions corresponding to the corrected details at the time of emitting the radiation from the radiation source 30. If the item corrected according to the user's command is the imaging posture, the radiation source control unit 32 controls the radiation source moving unit 38 to move the radiation source 30 so that the radiation source 30 is positioned at the position corresponding to the corrected imaging posture. Due to the process, the user may correct the imaging conditions in the current imaging without coming and going between the radiographic imaging room 42 and the site installed with the console 26.

When the exposure switch 34 is pushed by the user, the input of the exposure command is notified from the radiation generating apparatus 20 to the electronic cassette 22. In this case, a result of the determination of the step 302 becomes affirmative, and the process proceeds to the step 308. In a case where the received information is a notification of inputting of the exposure command received from the radiation generating apparatus 20, the process is branched from the step 308 to the step 320. If the exposure switch 34 is pushed, the radiation generating apparatus 20 emits the radiation from the radiation source 30. The radiation emitted from the radiation source 30 penetrates the patient (object to be imaged) to be irradiated on the electronic cassette 22. In the step 320, at the timing that the emitting of the radiation from the radiation source 30 is ended, the charges stored in the radiation detector 76 are read out and converted into the data of the radiographic image. The data of the radiographic image is stored in the image memory 104. The RIS information that the electronic cassette 22 receives from the console 26 includes the information (for example, the number of simultaneously-read lines, and the like) of defining the reading conditions in the reading of charges from the radiation detector 76, so that the reading of charges from the radiation detector 76 is performed according to the reading conditions defined by the information.

Figure 9A:
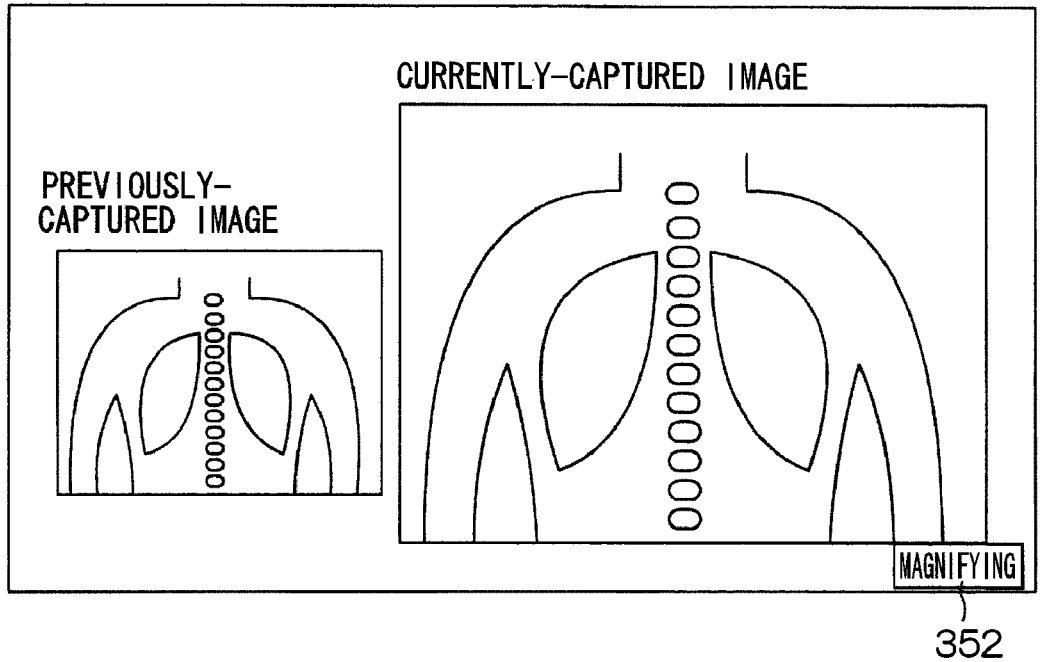
FIG. 9A is an image view illustrating an example of information displayed on a display surface of a display unit.

In the next step 322, for example, as shown in FIG. 9A, the radiographic image (previously-captured radiographic image associated with the current imaging) that is already displayed on the display unit 120 is reduced and displayed, and at the same time, the radiographic image (radiographic image obtained from the current imaging) indicated by the image data stored in the image memory 104 in the step 320 is displayed with a higher magnification ratio on the display unit 120. Therefore, by referring to the radiographic image newly displayed on the display unit 120, the user may check whether or not the imaging range of the current imaging is suitable and whether or not blur of the object to be imaged on the radiographic image occurs. In addition, by comparing the radiographic image obtained from the current imaging with the previously-captured radiographic image displayed simultaneously, the user may check again whether or not the imaging ranges of the two radiographic images are greatly different from each other.

In the step 322, the radiographic image in the data stored in the image memory 104 is displayed on the display unit 120 without no image processing, but not limited thereto. For example, after various kinds of image processing (for example, removing noise on the image data or various correction processes for correcting variation between pixels of the image data caused from variation in characteristics between pixel units 94 of the radiation detector 76) is performed on the image data, the processed image data may be displayed on the display unit 120. In the next step 324, the image data of the radiographic image obtained from the current imaging is transmitted to the console 26. The image data transmitted to the console 26 is stored in the storage unit 66C of the console 26 and displayed on the display 67 so as to be used for checking the radiographic image. At the same time, the image data is also transferred to the RIS server 14 to be stored in the RIS database and used for reading of the radiographic image or diagnosis and the like through the terminal 12. When the step 324 is ended, the process returns to the step 302, and the steps 302 to 306 are repeated.

Figure 9B:
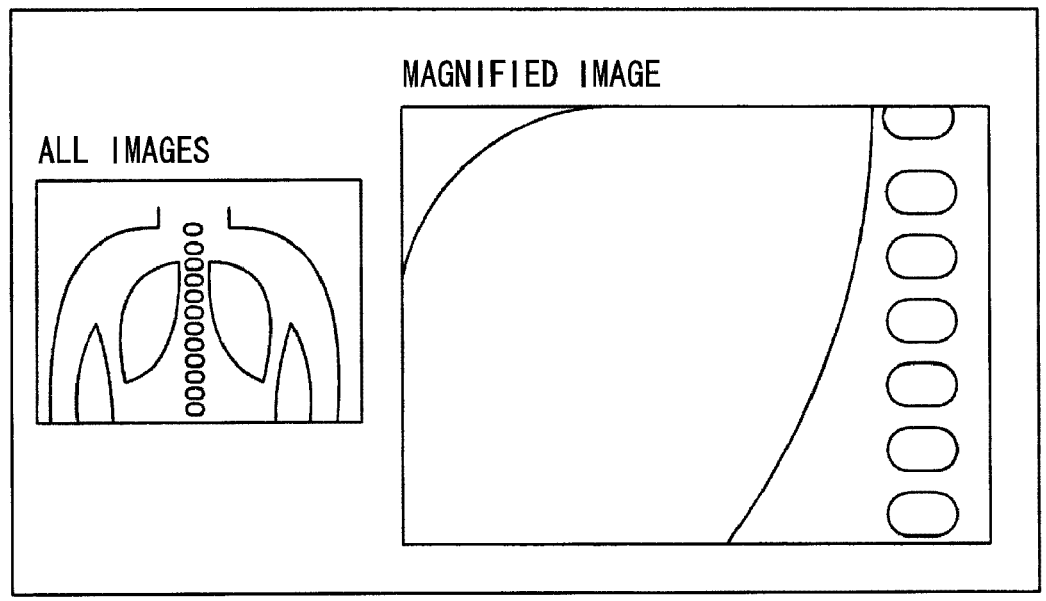
FIG. 9B is an image view illustrating an example of information displayed on a display surface of a display unit.

As shown in FIG. 9A, when the radiographic image obtained by the current imaging is displayed, a button 352 for commanding magnifying and displaying of the radiographic image is also displayed on the display surface of the display unit 120. In order to check details of some portion of the radiographic image obtained by the current imaging, after the user selects the button 352 to command the magnifying and displaying, the user performs a magnifying/displaying manipulation by pushing the position of the display surface corresponding to the position which is desired to be checked in detail. If the magnifying/displaying manipulation is performed, a result of the determination of the step 304 becomes affirmative, results of the determinations of the steps 326 and 330 become negative, and a result of the determination of the step 334 becomes affirmative. The process proceeds to the step 336. In the step 336, the magnified, displayed image in which the commanded portion is expanded with a higher magnification ratio is generated based on the data of the radiographic image stored in the image memory 104. After that, as shown in FIG. 9B, the previous image that is already displayed on the display unit 120 is erased, and the current image that is already displayed on the display unit 120 is reduced and displayed, so that the generated magnified, displayed image is displayed on the display unit 120. Accordingly, the user may check a desired portion in the radiographic image obtained from the current imaging in more detail.

The interface for displaying the magnified, displayed image is not limited to the aforementioned one. The interface of which magnification ratio may be designated by the user may be used. The interface in which scrolling of the display range of the magnified, displayed image may be commanded by the user may be used. If the step 336 is performed, the process proceeds to the step 338. In this case, a result of the determination becomes negative. The process returns to the step 302, and the steps 302 to 306 are repeated.

When the checking of the radiographic image displayed on the display unit 120 is ended, the user manipulates the input unit 108 configured with a touch panel to input the information indicating the ending of the checking of the radiographic image. In this case, a result of the determination of the step 304 becomes affirmative, results of the determinations of the steps 326, 330, 334 become negative, and a result of the determination of the step 338 becomes affirmative. The process proceeds to the step 340, in which the transmitting of the RIS information corresponding to to-be-next-performed imaging is requested to the console 26. The process returns to the step 302. In response to the request, the RIS information transmitted from the console 26 is received, and a series of the aforementioned steps are repeated.

In a case where the electronic cassette 22 is to be moved or in a case where all the capturing of the radiographic image scheduled on the date is ended, the user grasps the grip 128 and performs a manipulation of pressing the display unit 120 to be received in the casing 70 (the receiving portion 122 thereof) of the electronic cassette 22. If the manipulation is performed, the receiving of the display unit 120 is detected by the ejecting sensor 110, and a result of the determination of the step 306 becomes affirmative, so that the aforementioned information displaying process is ended.

In addition, as described above, if the request information is received from the electronic cassette 22, the RIS server 14 searches for the previously-captured radiographic image associated with the current imaging according to the search condition added to the received request information, but the invention is not limited thereto. The setting of the search condition of searching for the previously-captured radiographic image associated with the current imaging may be performed by the RIS server 14, based on the information (the information received from the terminal 12 added with the attribute information of the patient, the imaging date, or the like) which the RIS server 14 transmits to the console 26. In this case, there is no need for setting the search condition in the cassette control unit 106 of the electronic cassette 22, so that the load to the cassette control unit 106 may be lowered. In addition, for example, at the timing of receiving the request information for capturing the radiographic image from the terminal 12, adding the attribute information of the patient or the imaging date to the information received from the terminal 12, and transmitting the information to the console 26 of the radiographic imaging system 18, the RIS server 14 may set the search condition for the previously-captured radiographic image associated with the current imaging and perform searching for the radiographic image with the set search condition, and add the data of the radiographic image extracted through the searching to the information received from the terminal 12 to transmit the information to the console 26. In this case, since the electronic cassette 22 needs not to transmit the request information, the load to the cassette control unit 106 may be further lowered, and the traffic amount in the hospital intranet 16 may be suppressed.

In the aforementioned configuration, the data of the previously-captured radiographic image is stored in the storage unit 14A of the RIS server 14. Even in a case where a plurality of the electronic cassettes 22 are included in the RIS 10, since the data of the previously-captured radiographic images are managed in a unified manner by the RIS server 14, the aforementioned configuration is very suitable for the RIS 10 of a large-scale hospital where a plurality of the radiographic imaging rooms 42 are provided. On the other hand, in the invention, in a small-scale hospital where one radiographic imaging room 42 is provided, since the number of the electronic cassettes 22 disposed in the hospital is also small (for example, 1), the image memory 104 of the electronic cassette 22 may be configured with a non-volatile storage unit having a relatively large storage capacity so that the data of the previously-captured radiographic images are stored in the image memory 104 of the electronic cassette 22. In the exemplary embodiment, in a case where the previously-captured radiographic image associated with the current imaging is to be displayed on the display unit 120, the setting of the search condition for the radiographic image, and the searching, and the reading of data from the image memory 104 are performed by the cassette control unit 106, and after that, the previously-captured radiographic image associated with the current imaging is displayed on the display unit 120.

Figure 10:
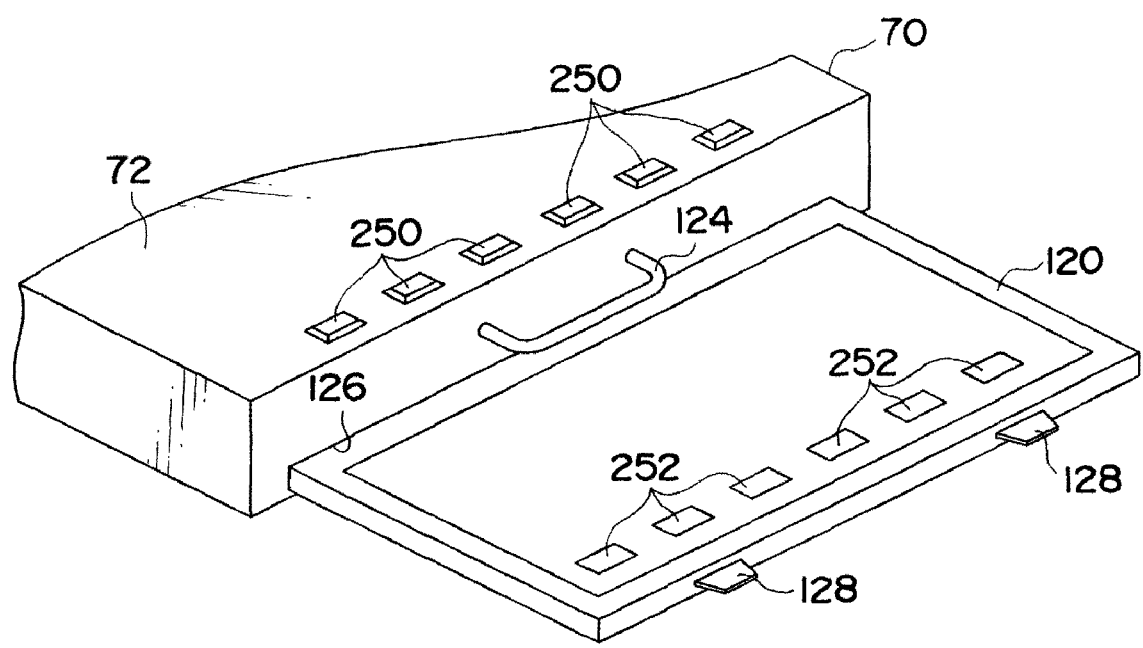
FIG. 10 is a perspective view illustrating another configuration of an input unit.

In addition, as described above, the input unit 108 through which the user inputs information is configured with a touch panel, but the invention is not limited thereto. For example, as shown in FIG. 10, a plurality of the switches 250 may be disposed to the casing 70 of the electronic cassette 22, and a guide mark 252 which indicates a function allocated to the each of the switches 250 with a letter is displayed to each of the switches 250 on the display surface of the display unit 120, so that the function (which is clearly indicated by each of the guide marks 252) allocated to the each of the switches 250 may be changed over every scene (for example, every window shown in FIGS. 8A to 8C, 9A and 9B). When one of the switches 250 is pushed, it is determined that the function allocated to the pushed switch 250 is commanded to be performed, and the corresponding process may be performed.

In addition, as an example of the display unit according to the invention, described is the display unit 120 having a flat rectangular parallelepiped shape and a configuration that the display unit may slidingly move along a straight line between the position where the display surface is expanded outside the casing 70 and the position where the display unit is received into the receiving portion 122 of the casing 70. However, any configuration capable of display an image may be used for the display unit according to the invention. For example, the display unit may have a configuration that the display unit may be rotated between the position where the display surface is expanded outside the casing 70 and the position where the display unit is received into the receiving portion 122 of the casing 70. The display unit may have a shape of a flexible sheet such as an electronic paper and a configuration that the display unit may be wound about a winding axis so as to be received into a receiving portion. The display unit may have a configuration that the display surface may be folded in a small size in the so-called "Miura Folding" shape or a concertina shape. In addition, the display unit is not limited to the configuration having a display surface of displaying an image. For example, as shown in FIGS. 11A and 11B, a configuration for emitting a projecting light for projecting the to-be-displayed information so as to project image on the to-be-projected object irradiated with the projecting light may be used for the display unit.

Figure 11A:
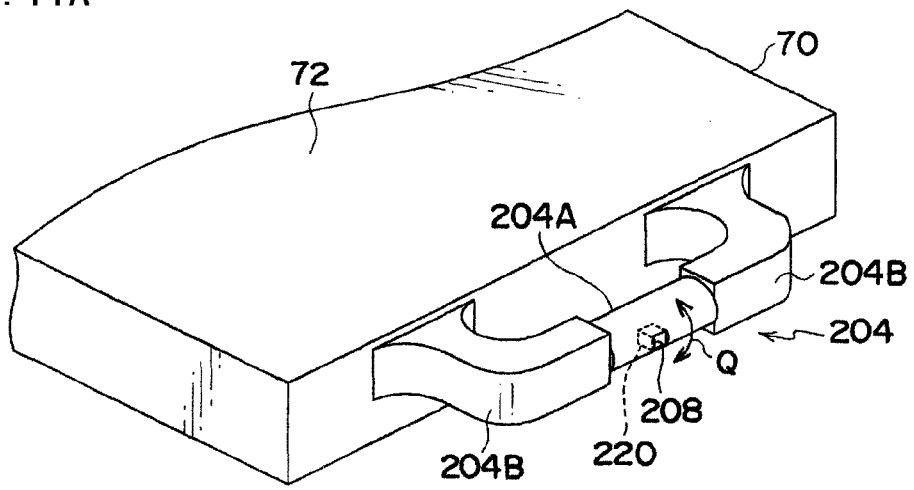
FIG. 11A is a perspective view illustrating another configuration of a display unit.
Figure 11B:
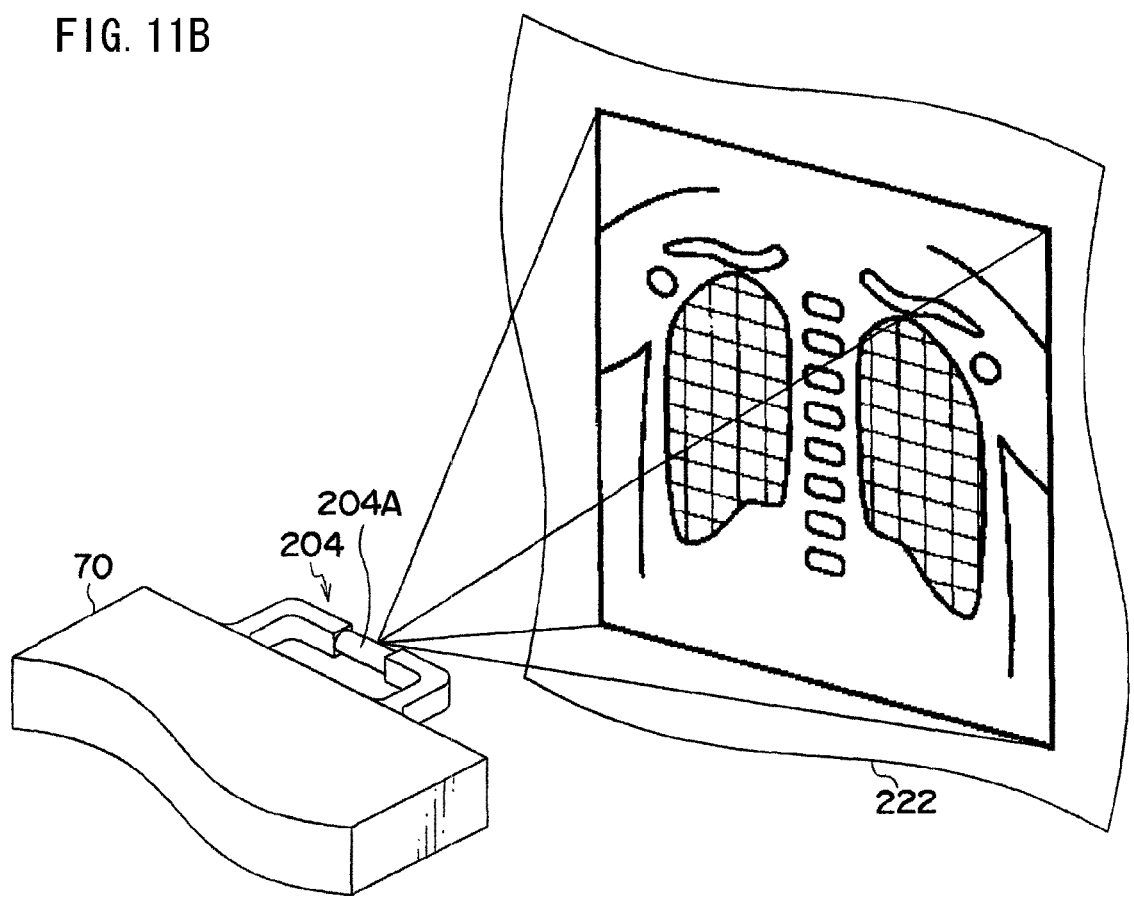
FIG. 11B is a perspective view illustrating still another configuration of a display unit.

In the example shown in FIGS. 11A and 11B, in the handle 204 provided at the casing 70 of the electronic cassette 22, a grip 204A grasped at the time of carrying the casing 70 is supported by a pair of base portions 204B provided at the longitudinal ends of the grip 204A so as to be rotated about a longitudinal-direction axis of the grip 204A (the direction of arrow Q in FIG. 11A). In addition, an emitting hole 208 is punctured at a central portion of the grip 204A, so that the projecting light for projecting to-be-displayed information is emitted through the emitting hole 208 on the position corresponding to the emitting hole 208 in the grip 204A. Therefore, the projector device 220 may project the to-be-displayed information onto the projected object irradiated with the emitted projecting light. Since the projector device 220 is rotated integrally with the grip 204A at the time of the rotating of the grip 204A, the emitting direction of the projecting light from the handle 204 may be changed according to the rotation of the grip 204A.

As the projector device 220, an ultra-small-sized projector device such as a DLP (digital light processing) Pico (a registered trade mark) (manufactured by Texas Instrument, USA) may be used. The device is embedded with an ultra-small-sized DMD (digital micro mirror device). The projecting light may be generated and emitted by individually driving mirrors two-dimensionally arrayed on the DMD. In addition, as the projector device 220, an ultra-small-sized LCD projector device using a small-sized high temperature poly-silicon TFT LCD panel (high temperature poly-silicon; HTPS) may be used. Instead of a modulation device such as a DMD or an acoustooptical device, a projector device having a configuration of modulating a semiconductor laser as a light source may be used (for example, refer to Nikkei BP, "a small-sized color projector that is miniaturized in a cigarette case size by Nippon Signal Co., Ltd, in Micromachine Conference"; on-line, searched on August 14, Heisei 20, Internet <URL: http://techon.nikkeibp.co.jp/article/NEWS/20080731/155810/>).

When receiving a command of projecting the radiographic image by the projector device 220, the cassette control unit 106 converts the image data of the to-be-projected radiographic image into a modulation data which may be used for modulation in the projector device 220 and outputs the converted data to the projector device 220. Therefore, the projector device 220 generates the modulated projecting light according to the modulation data input from the cassette control unit 106 and emits the generated projecting light through the emitting hole 208 to the outside of the grip 204A (the outside of the handle 204). When the projecting light is emitted through the emitting hole 208, the user adjusts the emitting direction of the projecting light from the handle 204 by rotating the grip 204A so that the projecting light is irradiated on the projected object 222 (refer to FIG. 11B) such as a wall or a screen (or a user's palm). Accordingly, the projecting light is irradiated on the projected object 222, so that the radiographic image is projected to be displayed on the projected object 222, as shown in FIG. 11B. The display unit according to the invention may be configured in the aforementioned projecting unit.

What is claimed is:

1. A portable radiographic imaging apparatus comprising:
   an image output unit which detects a radiation which penetrates an object to be imaged and is irradiated onto a surface of a casing of the portable radiographic imaging apparatus, and outputs data of a radiographic image which represents a distribution of an amount of irradiated radiation;
   a first storage unit which stores the data of the radiographic image output from the image output unit;
   a display unit which displays an image; and
   a display control unit that causes the display unit to display a previously captured radiographic image associated with a current imaging, before the object to be imaged is imaged, after receiving a request to display the previously captured radiographic image,
   wherein data of previously captured radiographic images is stored in the first storage unit, and wherein the display control unit searches the data of the previously captured radiographic images stored in the first storage unit for the data of the previously captured radiographic image associated with the current imaging, reads out from the first storage unit the data of the previously captured radiographic image extracted by the searching, and causes the display unit to display the read out data as the previously captured radiographic image associated with the current imaging.

2. The portable radiographic imaging apparatus of claim 1, wherein the display control unit sets a condition of the previously captured radiographic image associated with the current imaging based on attribute information indicating an attribute of the current imaging, and searches for the data of the previously captured radiographic image associated with the current imaging based on the set condition.

3. The portable radiographic imaging apparatus of claim 1, wherein the previously captured radiographic image associated with the current imaging is obtained by previously imaging the same imaged portion of the same object to be imaged as that of the current imaging.

4. The portable radiographic imaging apparatus of claim 1, wherein the previously-captured radiographic image associated with the current imaging is obtained by previously imaging the same imaged portion of an object to be imaged as that of the current imaging.

5. The portable radiographic imaging apparatus of claim 1, further comprising an input unit for inputting information, wherein when there are a plurality of previously captured radiographic images associated with the current imaging, the display control unit causes the display unit to reduce respective sizes of the plurality of previously captured radiographic images and to display the plurality of previously captured radiographic images in parallel, and if information is input via the input unit that indicates that one of the plurality of previously captured radiographic images displayed in parallel is selected, the display control unit causes the display unit to magnify and display the selected previously captured radiographic image.

6. The portable radiographic imaging apparatus of claim 1, wherein the display unit has a display surface that is configured to display an image and that is expandable outside the casing, and wherein the display unit is disposed with respect to the casing so that the display surface can be accommodated inside the casing or folded up.

7. The portable radiographic imaging apparatus of claim 1, wherein the display unit is a projecting unit that emits a projecting light for projecting and displaying information of an object to be displayed, so that the information of the object to be displayed is projected and displayed on an object irradiated with the projecting light.

8. A portable radiographic imaging apparatus comprising:
- an image output unit which detects a radiation which penetrates an object to be imaged and is irradiated onto a surface of a casing of the portable radiographic imaging apparatus, and outputs data of a radiographic image which represents a distribution of an amount of irradiated radiation;
- a first storage unit which stores the data of the radiographic image output from the image output unit;
- a display unit which displays an image;
- a display control unit that causes the display unit to display a previously captured radiographic image associated with a current imaging, before the object to be imaged is imaged, after receiving a request to display the previously captured radiographic image; and
- a communication unit configured to communicate with a radiographic image management apparatus having a second storage unit which stores data of previously captured radiographic images, wherein the display control unit sets a condition of the previously captured radiographic image associated with the current imaging based on attribute information indicating an attribute of the current imaging, notifies the radiographic image management apparatus of the set condition via the communication unit, and requests the radiographic image management apparatus to transmit the data of the previously captured radiographic image associated with the current imaging, and wherein the display control unit receives, from the radiographic image management apparatus via the communication unit, data of the previously captured radiographic image associated with the current imaging from among the data of the previously captured radiographic images stored in the management apparatus, and causes the display unit to display the received data as the previously captured radiographic image associated with the current imaging.

* * * * *